United States Patent
Lee et al.

(10) Patent No.: US 11,162,117 B2
(45) Date of Patent: Nov. 2, 2021

(54) WHOLE-CELL CATALYTIC SYSTEM AND APPLICATIONS THEREOF

(71) Applicant: National Taiwan University, Taipei (TW)

(72) Inventors: Kung-Ta Lee, Taipei (TW); Shan-Chi Hsieh, Taipei (TW); Ching-Yeuh Su, Taipei (TW); Yu-Chen Lai, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 188 days.

(21) Appl. No.: 16/192,207

(22) Filed: Nov. 15, 2018

(65) Prior Publication Data

US 2019/0284589 A1  Sep. 19, 2019

(30) Foreign Application Priority Data

Mar. 19, 2018  (TW) .................. 107109303

(51) Int. Cl.
| | | |
|---|---|---|
| *C12P 7/64* | (2006.01) | |
| *C07K 14/21* | (2006.01) | |
| *C12N 1/20* | (2006.01) | |
| *C12R 1/01* | (2006.01) | |
| *C07K 14/79* | (2006.01) | |

(52) U.S. Cl.
CPC ............ *C12P 7/6436* (2013.01); *C07K 14/21* (2013.01); *C07K 14/79* (2013.01); *C12N 1/205* (2021.05); *C12Y 118/01002* (2013.01); *C12R 2001/01* (2021.05); *C12Y 114/15003* (2013.01)

(58) Field of Classification Search
CPC .......... C07K 14/79; C07K 14/02; C12R 1/01; C12P 7/6439; C12P 7/6436; C12Y 118/01002; C12Y 114/15003
See application file for complete search history.

(56) References Cited

U.S. PATENT DOCUMENTS

| 9,200,043 B2 * | 12/2015 | Potter .................... C12P 7/6436 |
| 2008/0293060 A1 * | 11/2008 | Schirmer ............ C12N 15/1086 435/6.11 |
| 2016/0130616 A1 * | 5/2016 | Schirmer ....... C12Y 114/14001 524/599 |

OTHER PUBLICATIONS

Scheps et.al., Synthesis of w-hydroxy dodecanoic acid based on an engineered CYP153A fusion construct, Microbial Biotechnology, Feb. 2013, vol. 6—Issue 6, pp. 694-707 (Year: 2013).*
Hsieh et. al. Production of 1-Dodecanol, 1-Tetradecanol, and 1,12-Dodecanediol through Whole-Cell Biotransformation in *Escherichia coli*, Feb. 2018, Applied and Environmental Microbiology vol. 84—Issue 4, pp. 01806-01817 (Year: 2018).*
Liang et. al. Regulation of the Alkane Hydroxylase CYP153 Gene in a Gram-Positive Alkane-Degrading Bacterium, *Dietzia* sp. Strain DQ12-45-1b, Jan. 2016, Applied and Environmental Microbiology, vol. 82—Issue 2, pp. 608-619 (Year: 2016).*
Genbank Accession No. CP000514 Jan. 2014 (Year: 2014).*
Scheps et. al. Regioselective x-hydroxylation of medium-chain n-alkanes and primary alcohols by CYP153 enzymes from *Mycobacterium* marinum and *Polaromonas* sp. strain JS666, Jun. 2011, Organic & Bimolecular Chemistry, vol. 9, 6727-6733 (Year: 2011).*
Nie et. al. The Genome of the Moderate Halophile Amycolicicoccus subflavus DQS3-9A1T Reveals Four Alkane Hydroxylation Systems and Provides Some Clues on the Genetic Basis for Its Adaptation to a Petroleum Environment, Aug. 2013, Pios One, vol. 8—Issue 8, pp. 1-11 (Year: 2013).*
Mournier et. al. AupA and AupB Are Outer and Inner Membrane Proteins Involved in Alkane Uptake in Marinobacter hydrocarbonoclasticus SP17, Jun. 2018, American Society of Microbiology, vol. 9—Issue 3, 1-15 (Year: 2018).*
Ratajczak et. al. Expression of Alkane Hydroxylase from *Acinetobacter* sp. Strain ADP1 Is Induced by a Broad Range of n-Alkanes and Requires the Transcriptional Activator AlkR, Nov. 1998, Journal of Bacteriology, vol. 180, 5822-5827 (Year: 1998).*
Julsing et al. Outer Membrane Protein AlkL Boosts Biocatalytic Oxyfunctionalization of Hydrophobic Substrates in *Escherichia coli*, Aug. 2012, Applied and Environmental Microbiology, vol. 78—Issue 16, 5724-5733 (Year: 2012).*
Nie et. al. Characterization of a CYP153 alkane hydroxylase gene in a Gram-positive *Dietzia* sp. DQ12-45-1 b and its "team role" with alkW1 in alkane degradation. 2014. Applied Microbiology and Biotechnology vol. 98, pp. 163-173 (Year: 2014).*
Shan-Chi Hsieh et al., "1,12-Dodecanediol production by recombinant *E. coli*" and "Production of 1-dodecanol, 1-tetradecanol, and 1,12-dodecanediol by whole-cell biotransformation in *Escherichia coli*", AEM Accepted Manuscript Posted Online Nov. 27, 2017.
Scheps et al., "Synthesis of w-hydroxy dodecanoic acid based on an engineered CYP153A fusion construct" Microb Biotechnol. Nov. 2013; 6(6):694-707.

* cited by examiner

Primary Examiner — Neil P Hammell
Assistant Examiner — Tiffany Nicole Grooms
(74) Attorney, Agent, or Firm — WPAT, PC

(57) ABSTRACT

Provided is a method of activating gene expression using a protein having 90% or more sequence identity to SEQ ID NO:45. The protein activates the expression of a gene upon induction with a medium-chain or long-chain alkane or a medium-chain or long-chain fatty acid methyl ester. Also provided is a whole-cell catalytic system regulated by a medium-chain or long-chain alkane or a medium-chain or long-chain fatty acid methyl ester. The system includes a recombinant microbial cell expressing the protein and an alkane monooxygenase. Also provided is a method of preparing a medium-chain or long-chain alkane terminal oxidation product using the whole-cell catalytic system.

12 Claims, 18 Drawing Sheets
Specification includes a Sequence Listing.

SEQUENCE LISTING

<160> NUMBER OF SEQ ID NOS: 45

<210> SEQ ID NO 1
<211> LENGTH: 1071
<212> TYPE: DNA
<213> ORGANISM: Marinobacter aquaeoli VT8

<400> SEQUENCE: 1

| | | | | | |
|---|---|---|---|---|---|
| ttaatcacgt | gtatagatgg | tgtgtgatct | gacgtttagc | ctgaattgct | caggtggctg | 60 |
| gccaaaccag | cgtttgaagg | cgcgtctgaa | attggcactg | tcgtgataat | tcatcaacgc | 120 |
| ggcaatggcc | tcgattgaca | gttcgctgtc | acgcaggtat | agcgctgcct | gctgagacag | 180 |
| aatctcgtca | cggattttc | gaaaactgct | gccttcatgg | ttgagtttac | gcgccagggt | 240 |
| gcgtttgctg | atgaacagag | aagcagccgc | ttcctcttca | ctgagcgttc | ccggcggccg | 300 |
| ggacaacatc | atcttcttca | gccgggtctg | gtagcttggc | ttatcggact | gaagttgcgc | 360 |
| aagcatggct | tcacactgtc | gcatggccag | atgatagttt | tcatgattgg | cagaggcgtt | 420 |

```
tggttcccga cacaaggcca tcggcaagct gagttttaat tggctgcaat caaagtgaat    480
ctgcccggac aaaaagtccg aatacgttgc gtgatactcg ggtttcggat gggcaaagca    540
tacttcagcc tcgcgcaaag ggcggccaac catgaactcg ccgaattcga aaagtgcctt    600
gaccatcgca tccgacaggc aacgctgtat gtcatcgtct aatggcccca ggtactgcag    660
aatacattcc aaacgctcac cgacttgctg caagtgcaac tggatgaagc tcgcgcgcgt    720
gggcaggaat gtccgaatcg cgtgtagagc agtgaggagg tcggggctgc tgtaagccac    780
gaacccattt gctccgtggg ttgccggagt cattcgttta cccagcctta acccaaattc    840
tggctggccg acagatccaa ttgcattacg caggatctgt atctgctgag ccacagtaag    900
cagtccgtcc tcgctcaaaa attgcgtcac cccaagtcca gtgccccgca gcagacgcgg    960
aagttgtctg gctgtcagat tcagctcacg tgcaactagc cgtgagtaat tcgatggaat   1020
atccggaccg ggactttgca actcctccat tttcttccgc gccgccatca t            1071
```

<210> SEQ ID NO 2
<211> LENGTH: 14
<212> TYPE: PRT
<213> ORGANISM: Artificial sequence
<220> FEATURE:
<223> OTHER INFORMATION: AlkR protein fragment 80-93

<400> SEQUENCE: 2

Gly Leu Arg Leu Gly Lys Arg Met Thr Pro Ala Thr His Gly
1               5                   10

<210> SEQ ID NO 3
<211> LENGTH: 17
<212> TYPE: PRT
<213> ORGANISM: Artificial sequence
<220> FEATURE:
<223> OTHER INFORMATION: AlkR protein fragment 194-209

<400> SEQUENCE: 3

Leu Ser Gly Gln Ile His Phe Asp Cys Ser Gln Leu Lys Leu Ser Leu
1               5                   10                  15

Pro

<210> SEQ ID NO 4
<211> LENGTH: 14
<212> TYPE: PRT
<213> ORGANISM: Artificial sequence
<220> FEATURE:
<223> OTHER INFORMATION: AlkR protein fragment 278-291

<400> SEQUENCE: 4

Thr Leu Ala Arg Lys Leu Asn His Glu Gly Ser Ser Phe Arg
1               5                   10

<210> SEQ ID NO 5
<211> LENGTH: 20
<212> TYPE: PRT
<213> ORGANISM: Artificial sequence
<220> FEATURE:
<223> OTHER INFORMATION: AlkR protein fragment 316-335

<400> SEQUENCE: 5

Ile Ala Ala Leu Met Asn Tyr His Asp Ser Ala Asn Phe Arg Arg Ala
1               5                   10                  15

Phe Lys Arg Trp
            20

<210> SEQ ID NO 6
<211> LENGTH: 1413
<212> TYPE: DNA
<213> ORGANISM: Marinobacter aquaeoli VT8

<400> SEQUENCE: 6

```
atgccaacac tgcccagaac atttgacgac attcagtccc gactgattaa cgccacctcc      60
agggtggtgc cgatgcagag gcaaattcag ggactgaaat tcttaatgag cgccaagagg     120
aagaccttcg gcccacgccg accgatgccc gaattcgttg aaacaccat cccggacgtt     180
aacacgctgg cccttgagga catcgatgtc agcaatccgt ttttataccg gcagggtcag     240
tggcgcgcct atttcaaacg gttgcgtgat gaggcgccgg tccattacca aagaacagc     300
cctttcggcc ccttctggtc ggtaactcgg tttgaagaca tcctgttcgt ggataagagt     360
cacgacctgt tttccgccga ccgcaaatc attctcggtg accctccgga ggggctgtcg     420
gtggaaatgt tcatagcgat ggatccgccg aaacacgatg tgcagcgcag ctcggtgcag     480
ggagtagtgg caccgaaaaa cctgaaggag atggaggggc tgatccgatc acgcaccggc     540
gatgtgcttg acagcctgcc tacagacaaa ccctttaact gggtacctgc tgtttccaag     600
gaactcacag gccgcatgct ggcgacgctt ctggattttc cttacgagga acgccacaag     660
ctggttgagt ggtcggacag aatggcaggt gcagcatcgg ccaccggcgg ggagtttgcc     720
gatgaaaatg ccatgtttga cgacgcggca gacatggccc ggtctttctc caggcttttgg    780
cgggacaagg aggcgcgccg cgcagcaggc gaggagcccg tttcgatttt gatcagcctg     840
ttgcagagca caaagaaac gaaagacctg atcaatcggc cgatggagtt tatcggtaat     900
ttgacgctgc tcatagtcgc cggcaacgat acgacgcgca actcgatgag tggtggcctg     960
gtggccatga acgaattccc cagggaattt gaaaaattga aggcaaaacc ggagttgatt    1020
ccgaacatgg tgtcggaaat catccgctgg caaacgccgc tggcctatat gcgccgaatc    1080
gccaagcagg atgtcgaact gggcggccag accatcaaga agggtgatcg agttgtcatg    1140
tggtacgcgt cgggtaaccg ggacgagcgc aaatttgaca ccccgatca gttcatcatt    1200
gatcgcaagg acgcacgaaa ccacatgtcg ttcggctatg ggttcaccg ttgcatgggc    1260
aaccgtctgg ctgaactgca actgcgcatc ctctgggaag aaatactcaa gcgttttgac    1320
aacatcgaag tcgtcgaaga gcccgagcgg gtgcagtcca acttcgtgcg gggctattcc    1380
aggttgatgg tcaaactgac accgaacagt taa                                 1413
```

<210> SEQ ID NO 7
<211> LENGTH: 312
<212> TYPE: DNA
<213> ORGANISM: Marinobacter aquaeoli VT8

<400> SEQUENCE: 7

```
atgggcggtc acgatgggcc ggaatatgca catgtcgcag aattcaaagc tggttcctcg      60
gtaatgcaaa tcgctgttga tagcgccatt cccggtatcg acggggattg tgggggggag     120
tgcgcctgcg gtacctgcca cgttatcgtc acgaacgaat ggttcagcaa gacaggcacg     180
cctggcaatg aggaagaaca aatgctgtca atgacaccgg agcgggcgag cacttcgcgc     240
ctgggctgcc aggtggtact gactgatgaa atggacggca tgaccgtgca tttacccgag     300
ttccagatgt ga                                                         312
```

<210> SEQ ID NO 8
<211> LENGTH: 1251

```
<212> TYPE: DNA
<213> ORGANISM: Marinobacter aquaeoli VT8

<400> SEQUENCE: 8
atggtaagca aacgtaaaga gaggacggtc attgttggcg gtgggcacgc agcaggtgcc      60
ctcctgacag ccttactcca aaaaaaatat caacatgagg tcgttctggt ggggaatgaa     120
cctcatccgc cctaccatcg accgccgctg tccaagaatt acctgacagg agacgttgat     180
caggagtcgc tgtacctgaa accgcgctcg gtatacgaga acgcaggcca tcagttgcgg     240
ctcggtgtgc gcgtcgaaca aattgatcgg gacagtagca ccatcagctt gtcggatcag     300
agcaggctgc aatacgatcg actggtcctg gccaccgggt cacaccttcg acacctgaac     360
gcgcccgggg ctgacttaaa tggcattcat tacctgcacg acatagctga ttcagaggta     420
ctgcgtgaac agttagttgc tggaaagcgc ctggtcgtcg tgggtggtgg ttacatcggc     480
cttgaggtgg cggccagtgc caacaaaaaa ggtgttaatg tcacggtgct agaagccgcc     540
gaacgtctta tgcagcgcgt tacgggcccg gaaatatcag cgttccttta cgacaaacac     600
cgtggcgccg gcgtggacgt acgtctgaac acagcggtaa ccggcttcga agcgggcgat     660
caggggcatg tggctggcgt gacgttggcg gacggaagca ccgtaccggc cgacatcgtc     720
cttgtgtcga tcggcattat cccggaaacc gctctggcta aggacgccgg cctgccctgt     780
gataacggta ttattgttga cgaatttacc cgtaccgagg accccgccat cttggcgatc     840
ggtgactgca cccggcaccg gaatctttc ttcgagaaga tgcaacgact cgagtctgtc     900
gccaatgctg tcgatcaggc tcgtacagcc gcggcaaccc tgatgggtga ggagaaaccc     960
tatgatagcg ttccatggtt ctggtcaaac cagtacgatg ttcgtctgca gatggtagga    1020
ttgtcgcaaa atcatgatca gcgagtggtt cgaggcaccc ccgaggataa aggatttgcc    1080
gtgttctatc tccgcgaagg ctgtgttatt gctgttgacg cggtcaacct gccccttgct    1140
tttttggtag gcaagacact cgttcaacaa cgcagaacga tcaacccgga actaatagag    1200
gatccggata ctgaactgaa atctttggtg aacggaaggc tccagagttg a             1251

<210> SEQ ID NO 9
<211> LENGTH: 43
<212> TYPE: DNA
<213> ORGANISM: Artificial sequence
<220> FEATURE:
<223> OTHER INFORMATION: Synthetic primer

<400> SEQUENCE: 9
gtttcttcta gaggcctaaa gaggagaaat actagatggc ttc                       43

<210> SEQ ID NO 10
<211> LENGTH: 32
<212> TYPE: DNA
<213> ORGANISM: Artificial sequence
<220> FEATURE:
<223> OTHER INFORMATION: Synthetic primer

<400> SEQUENCE: 10
gtttctggta ccattaccgc ctttgagtga gc                                   32

<210> SEQ ID NO 11
<211> LENGTH: 19
<212> TYPE: DNA
<213> ORGANISM: Artificial sequence
<220> FEATURE:
<223> OTHER INFORMATION: Synthetic primer
```

<400> SEQUENCE: 11
cctgcactgg ctccccaag                                                  19

<210> SEQ ID NO 12
<211> LENGTH: 27
<212> TYPE: DNA
<213> ORGANISM: Artificial sequence
<220> FEATURE:
<223> OTHER INFORMATION: Synthetic primer

<400> SEQUENCE: 12
cccgggacca gcattgatga ttgacag                                         27

<210> SEQ ID NO 13
<211> LENGTH: 28
<212> TYPE: DNA
<213> ORGANISM: Artificial sequence
<220> FEATURE:
<223> OTHER INFORMATION: Synthetic primer

<400> SEQUENCE: 13
gtttcttcta gagcactggc tccccaag                                        28

<210> SEQ ID NO 14
<211> LENGTH: 28
<212> TYPE: DNA
<213> ORGANISM: Artificial sequence
<220> FEATURE:
<223> OTHER INFORMATION: Synthetic primer

<400> SEQUENCE: 14
gatatcatgt tcgataaacg taactttg                                        28

<210> SEQ ID NO 15
<211> LENGTH: 29
<212> TYPE: DNA
<213> ORGANISM: Artificial sequence
<220> FEATURE:
<223> OTHER INFORMATION: Synthetic primer

<400> SEQUENCE: 15
caaactgaac atgtcgcaga attcaaagc                                       29

<210> SEQ ID NO 16
<211> LENGTH: 23
<212> TYPE: DNA
<213> ORGANISM: Artificial sequence
<220> FEATURE:
<223> OTHER INFORMATION: Synthetic primer

<400> SEQUENCE: 16
ttatcaactc tggagccttc cgt                                             23

<210> SEQ ID NO 17
<211> LENGTH: 24
<212> TYPE: DNA
<213> ORGANISM: Artificial sequence
<220> FEATURE:
<223> OTHER INFORMATION: Synthetic primer

<400> SEQUENCE: 17
cctaccagca ttgatgattg acag                                            24

<210> SEQ ID NO 18
<211> LENGTH: 37

<212> TYPE: DNA
<213> ORGANISM: Artificial sequence
<220> FEATURE:
<223> OTHER INFORMATION: Synthetic primer

<400> SEQUENCE: 18
gtttcttcta gagttaatct ttctgcgaat tgagatg       37

<210> SEQ ID NO 19
<211> LENGTH: 48
<212> TYPE: DNA
<213> ORGANISM: Artificial sequence
<220> FEATURE:
<223> OTHER INFORMATION: Synthetic primer

<400> SEQUENCE: 19
gtttctctgc agcggccgct aggcctatac gaccagtcta aaaagcgc       48

<210> SEQ ID NO 20
<211> LENGTH: 47
<212> TYPE: DNA
<213> ORGANISM: Artificial sequence
<220> FEATURE:
<223> OTHER INFORMATION: Synthetic primer

<400> SEQUENCE: 20
tcacacagga ctactagatg agttttttcta attataaagt aatcgcg       47

<210> SEQ ID NO 21
<211> LENGTH: 23
<212> TYPE: DNA
<213> ORGANISM: Artificial sequence
<220> FEATURE:
<223> OTHER INFORMATION: Synthetic primer

<400> SEQUENCE: 21
ttagaaaaca tatgacgcac caa       23

<210> SEQ ID NO 22
<211> LENGTH: 41
<212> TYPE: DNA
<213> ORGANISM: Artificial sequence
<220> FEATURE:
<223> OTHER INFORMATION: Synthetic primer

<400> SEQUENCE: 22
cgaattcgag ctcggtaccc tcaggcgatc ttcttcaaac c       41

<210> SEQ ID NO 23
<211> LENGTH: 29
<212> TYPE: DNA
<213> ORGANISM: Artificial sequence
<220> FEATURE:
<223> OTHER INFORMATION: Synthetic primer

<400> SEQUENCE: 23
atgttcggca ctggctgaag accggtgac       29

<210> SEQ ID NO 24
<211> LENGTH: 30
<212> TYPE: DNA
<213> ORGANISM: Artificial sequence
<220> FEATURE:
<223> OTHER INFORMATION: Synthetic primer

<400> SEQUENCE: 24
cttcagccag tgccgaacat gttcaggtac                                              30

<210> SEQ ID NO 25
<211> LENGTH: 38
<212> TYPE: DNA
<213> ORGANISM: Artificial sequence
<220> FEATURE:
<223> OTHER INFORMATION: Synthetic primer

<400> SEQUENCE: 25
gtcgactcta gaggatcccc atgcaagccg acttctgg                                     38

<210> SEQ ID NO 26
<211> LENGTH: 34
<212> TYPE: DNA
<213> ORGANISM: Artificial sequence
<220> FEATURE:
<223> OTHER INFORMATION: Synthetic primer

<400> SEQUENCE: 26
tcgagctcgg tacccatgtt aggtcagatg atgc                                         34

<210> SEQ ID NO 27
<211> LENGTH: 26
<212> TYPE: DNA
<213> ORGANISM: Artificial sequence
<220> FEATURE:
<223> OTHER INFORMATION: Synthetic primer

<400> SEQUENCE: 27
tctggagagc ggtgtgaata aagtac                                                  26

<210> SEQ ID NO 28
<211> LENGTH: 28
<212> TYPE: DNA
<213> ORGANISM: Artificial sequence
<220> FEATURE:
<223> OTHER INFORMATION: Synthetic primer

<400> SEQUENCE: 28
cacaccgctc tccagatgaa aagctttc                                                28

<210> SEQ ID NO 29
<211> LENGTH: 38
<212> TYPE: DNA
<213> ORGANISM: Artificial sequence
<220> FEATURE:
<223> OTHER INFORMATION: Synthetic primer

<400> SEQUENCE: 29
ctctagagga tccccttatt cacagacaga agaactac                                     38

<210> SEQ ID NO 30
<211> LENGTH: 38
<212> TYPE: DNA
<213> ORGANISM: Artificial sequence
<220> FEATURE:
<223> OTHER INFORMATION: Synthetic primer

<400> SEQUENCE: 30
cgaattcgag ctcggtaccc cgctgttgct tggggcgc                                     38

<210> SEQ ID NO 31
<211> LENGTH: 49
<212> TYPE: DNA
<213> ORGANISM: Artificial sequence

```
<220> FEATURE:
<223> OTHER INFORMATION: Synthetic primer

<400> SEQUENCE: 31
aggcaaacat tggtgttct ccaattttta ttaaattagt cgctacgag          49

<210> SEQ ID NO 32
<211> LENGTH: 28
<212> TYPE: DNA
<213> ORGANISM: Artificial sequence
<220> FEATURE:
<223> OTHER INFORMATION: Synthetic primer

<400> SEQUENCE: 32
gcgcatctga ttatgtgagc acgcagag                               28

<210> SEQ ID NO 33
<211> LENGTH: 42
<212> TYPE: DNA
<213> ORGANISM: Artificial sequence
<220> FEATURE:
<223> OTHER INFORMATION: Synthetic primer

<400> SEQUENCE: 33
gtcgactcta gaggatcccc gtcaaattgt tattttgcgt tg               42

<210> SEQ ID NO 34
<211> LENGTH: 28
<212> TYPE: DNA
<213> ORGANISM: Artificial sequence
<220> FEATURE:
<223> OTHER INFORMATION: Synthetic primer

<400> SEQUENCE: 34
agaacaccaa atgtttgcct cgctttcc                               28

<210> SEQ ID NO 35
<211> LENGTH: 28
<212> TYPE: DNA
<213> ORGANISM: Artificial sequence
<220> FEATURE:
<223> OTHER INFORMATION: Synthetic primer

<400> SEQUENCE: 35
gctcacataa tcagatgcgc tgggtgtc                               28

<210> SEQ ID NO 36
<211> LENGTH: 34
<212> TYPE: DNA
<213> ORGANISM: Artificial sequence
<220> FEATURE:
<223> OTHER INFORMATION: Synthetic primer

<400> SEQUENCE: 36
acttcttcat aattctctct ccggtatact tttc                        34

<210> SEQ ID NO 37
<211> LENGTH: 38
<212> TYPE: DNA
<213> ORGANISM: Artificial sequence
<220> FEATURE:
<223> OTHER INFORMATION: Synthetic primer

<400> SEQUENCE: 37
gtcgactcta gaggatcccc cactagtgct ttcccgag                    38
```

<210> SEQ ID NO 38
<211> LENGTH: 38
<212> TYPE: DNA
<213> ORGANISM: Artificial sequence
<220> FEATURE:
<223> OTHER INFORMATION: Synthetic primer

<400> SEQUENCE: 38
cgaattcgag ctcggtaccc ggcgtgcacc tggcgctt        38

<210> SEQ ID NO 39
<211> LENGTH: 34
<212> TYPE: DNA
<213> ORGANISM: Artificial sequence
<220> FEATURE:
<223> OTHER INFORMATION: Synthetic primer

<400> SEQUENCE: 39
catggcttga caatgatgct cagccactcg aacc        34

<210> SEQ ID NO 40
<211> LENGTH: 28
<212> TYPE: DNA
<213> ORGANISM: Artificial sequence
<220> FEATURE:
<223> OTHER INFORMATION: Synthetic primer

<400> SEQUENCE: 40
agcatcattg tcaagccatg aggccggg        28

<210> SEQ ID NO 41
<211> LENGTH: 34
<212> TYPE: DNA
<213> ORGANISM: Artificial sequence
<220> FEATURE:
<223> OTHER INFORMATION: Synthetic primer

<400> SEQUENCE: 41
cggagagaga attatgaaga agtggcaatg cgtg        34

<210> SEQ ID NO 42
<211> LENGTH: 1134
<212> TYPE: DNA
<213> ORGANISM: Pseudomonas aeruginosa PAO1

<400> SEQUENCE: 42
atgtttgcct cgctttcctc tgcctggatg ctgcgtctga aaaagtacgg ctactggatc        60
tggctgatcg cggtgctcgg catcccgctc agctactggt ggtcgctcgg tagcgactac        120
cccaacgcct ggccctggct ggtgatcagc gtggtgttcg ggctgatccc gatcctcgat        180
gccatcgtcg gccgcgatcc ggccaacccc gaggaagcca gcgaagtgcc ggagatggaa        240
gcacagggct actaccgcgt actgtccctg gccaccgtcc cgctgttgct gggcatgctc        300
gtctggtccg gctggatcct cgcccacgag cccgctgggg actgggtcgg ccaactgggc        360
tggatcctgt cggtgggcac cgtgatgggc gccatcggca tcaccgtctc ccacgaactg        420
atccacaagg acccgcaact ggaacagaac gccggcggcc tgctgctggc ggcggtgtgc        480
tatgccggct tcaaggtcga acacgtgcgc ggccaccatg tacacgtctc gaccccggaa        540
gatgcctcgt cctcgcgcta cggccagagc ctctactcgt tcctcccgca cgcctacaag        600
cacaacttcc tcaacgcctg gcgcctggag gccgagcgcc tgaagcgcaa gggcctgccg        660
gccctgcact ggcgcaacga gctgatctgg tggtacgcca tcagcgccct cttcctgctc        720

```
ggcttcagcc tggccttcgg ctggctggga gcgatcttct tcctcggcca gtcggtgatg    780
gccttcaccc tgctggagat cgtcaactac gtcgagcact acggcctgca tcggcggcgc    840
ctggacaacg ccgctacga acgcaccacg ccggaacact cgtggaacag caatttcctc    900
ctgaccaacc tgttcctttt ccacctgcag cgccattccg accaccatgc ctacgccaag    960
cgccgctacc aggtgctgcg ccactacgac agcagcccgc aactgcccaa cggctatgcc   1020
gggatgatcg tcctcgccct gttcccaccg ctctggcgcg cggtgatgga cccgaaggtg   1080
cgcgcctact atgccggcga ggaataccag cttaccgaca cccagcgcat ctga         1134
```

<210> SEQ ID NO 43
<211> LENGTH: 519
<212> TYPE: DNA
<213> ORGANISM: Pseudomonas aeruginosa PAO1

<400> SEQUENCE: 43

```
atgaagaagt ggcaatgcgt ggtgtgtgga ctgatctatg acgaggccaa aggctggccg     60
gaagaaggca tcgaggcggg aacgcgctgg gaagacgtgc ctgaagactg ctgtgccccc    120
gactgcggcg tcggcaagct ggacttcgag atgatcgaaa tcggctgagc cccgctcgcc    180
ggcgaagaag gcggccctgg ccgccttttt tcatgcctgg ccagcggccg tccaggagtt    240
atccttggga cttgggtccg gtcattgact gtcctgccgg aacgcccgg cagccttgcc     300 gttggccggc caccgacgct gagctaggtt cgacgaacga ggagggtggc tatgcgcaag    360 tgcaatgcg tggtctgcgg cttcatctac gacgaagccc tgggcctgcc cgaagaaggc    420
attccggcgg gaacccgttg ggaggacatc ccggcggact gggtctgccc ggactgcggt    480
gtcggcaaga tcgatttcga gatgatcgag atcgcctga                           519
```

<210> SEQ ID NO 44
<211> LENGTH: 1155
<212> TYPE: DNA
<213> ORGANISM: Pseudomonas aeruginosa PAO1

<400> SEQUENCE: 44

```
atgagcgagc gtgcgcccct ggtaatcatc ggaaccggcc tggcgggcta caacctggcc     60
cgcgagtggc gcaagctgga cggcgagacg ccgctgctga tgatcaccgc cgacgacggc    120
cgttcctatt ccaagccgat gctctctacc ggcttctcga agaacaagga cgccgacggc    180
ctggccatgg ccgaaccggg cgccatggcc gagcaactga acgcgcgcat cctgacccat    240 accgggtca ccggtatcga tcccggccat cagcggatct ggatcggcga ggaagaggtg     300
cgttatcgcg acctggtcct ggcctggggc gcggagccga tccgggtgcc ggtcgagggc    360 gatgccag acgcgctcta cccgatcaac gacctggaag actacgcgcg cttccgccag    420
gcggctgccg gcaagcgccg ggtactgctg ctcggtgcgg ggctgatcgg ttgcgaattc    480
gccaacgacc tctccagcgg cggctaccag ctcgacgtgg tggcgccttg cgagcaggtc    540
atgccgggcc tgctccaccc ggccgcggcg aaggccgtgc aggcaggcct ggaaggcctc    600
ggcgtgcgct tccacctggg gccggtgctg ccagcctga agaaggccgg cgaggggctg    660
gaagcgcatc tttcggatgg cgaggtgatt ccctgcgacc tggtggtctc cgccgtcggc    720
ctgcgtccgc gcaccgaact ggccttcgcc gccgggctgg cggtcaaccg cgggatcgtc    780
gtcgaccgct cgctgcgcac ctcccacgcc aacatctacg cgctgggcga ctgcgccgaa    840
gtggacggcc tcaacctgct ctatgtgatg ccgctgatgg cctgcgcacg cgccctggcg    900
```

```
cagaccctcg ccggcaaccc cagccaggtg gcctacggtc ccatgccggt gacggtgaag    960 acccccggcct gcccgctggt ggtgtcgccg ccgccccgcg gaatggatgg ccaatggcta   1020
gtggaaggct ctggaacgga cctcaaggtc ctgtgtcggg ataccgctgg tcgagtgatc   1080
ggttatgccc tgaccggagc ggcggtgaac gaaaaattgg ccctgaacaa agagttaccc   1140
ggcctcatgg cttga                                                    1155
```

<210> SEQ ID NO 45
<211> LENGTH: 356
<212> TYPE: PRT
<213> ORGANISM: Marinobacter aquaeoli VT8

<400> SEQUENCE: 45

```
Met Met Ala Ala Arg Lys Lys Met Glu Glu Leu Gln Ser Pro Gly Pro
1               5                   10                  15

Asp Ile Pro Ser Asn Tyr Ser Arg Leu Val Ala Arg Glu Leu Asn Leu
            20                  25                  30

Thr Ala Arg Gln Leu Pro Arg Leu Leu Arg Gly Thr Gly Leu Gly Val
        35                  40                  45

Thr Gln Phe Leu Ser Glu Asp Gly Leu Leu Thr Val Ala Gln Gln Ile
    50                  55                  60

Gln Ile Leu Arg Asn Ala Met Asp Leu Ser Gly Gln Pro Glu Phe Gly
65                  70                  75                  80

Leu Arg Leu Gly Lys Arg Met Thr Pro Ala Thr His Gly Ala Met Gly
                85                  90                  95

Phe Val Ala Tyr Ser Ser Pro Asp Leu Leu Thr Ala Leu His Ala Ile
            100                 105                 110

Arg Thr Phe Leu Pro Thr Arg Ala Ser Phe Ile Gln Leu His Leu Gln
        115                 120                 125

Gln Val Gly Glu Arg Leu Glu Cys Ile Leu Gln Tyr Leu Gly Pro Leu
    130                 135                 140

Asp Asp Asp Ile Gln Arg Cys Leu Ser Asp Ala Met Val Lys Ala Leu
145                 150                 155                 160

Phe Glu Phe Gly Glu Phe Met Val Gly Arg Pro Leu Arg Glu Ala Glu
                165                 170                 175

Val Cys Phe Ala His Pro Lys Pro Glu Tyr His Ala Thr Tyr Ser Asp
            180                 185                 190

Phe Leu Ser Gly Gln Ile His Phe Asp Cys Ser Gln Leu Lys Leu Ser
        195                 200                 205

Leu Pro Met Ala Leu Cys Arg Glu Pro Asn Ala Ser Ala Asn His Glu
    210                 215                 220

Asn Tyr His Leu Ala Met Arg Gln Cys Glu Ala Met Leu Ala Gln Leu
225                 230                 235                 240

Gln Ser Asp Lys Pro Ser Tyr Gln Thr Arg Leu Lys Lys Met Met Leu
                245                 250                 255

Ser Arg Pro Pro Gly Thr Leu Ser Glu Glu Ala Ala Ala Ser Leu
            260                 265                 270

Phe Ile Ser Lys Arg Thr Leu Ala Arg Lys Leu Asn His Glu Gly Ser
        275                 280                 285

Ser Phe Arg Lys Ile Arg Asp Glu Ile Leu Ser Gln Gln Ala Ala Leu
    290                 295                 300

Tyr Leu Arg Asp Ser Glu Leu Ser Ile Glu Ala Ile Ala Ala Leu Met
305                 310                 315                 320

Asn Tyr His Asp Ser Ala Asn Phe Arg Arg Ala Phe Lys Arg Trp Phe
```

```
                    325                 330                 335
Gly Gln Pro Pro Glu Gln Phe Arg Leu Asn Val Arg Ser His Thr Ile
                340                 345                 350
Tyr Thr Arg Asp
        355
```

WHOLE-CELL CATALYTIC SYSTEM AND APPLICATIONS THEREOF

CROSS-REFERENCE TO RELATED APPLICATION

This application claims priority of Taiwan patent application No. 107109303, filed on Mar. 19, 2018, the content of which is incorporated herein in its entirety by reference.

BACKGROUND OF THE INVENTION

1. Field of the Invention

The present invention relates to the applications of a protein and a whole-cell catalytic system including the protein, and the whole-cell catalytic system. Particularly, the present invention relates to a method of activating gene expression using an alkane response protein, a whole-cell catalytic system including the alkane response protein, and a method of preparing a medium-chain or long-chain alkane terminal oxidation product using the whole cell catalytic system.

2. The Prior Art

The terminal oxidation products of medium/long-chain straight alkanes, such as medium/long-chain alkanediols and medium/long-chain alkanedioic acids, are widely applied in the industry, for example, as lubricants, surfactants, and detergents. However, the chemical inertness of alkanes makes it difficult to carry out a regioselective oxyfunctionalization. At present, primary alkanols are mostly obtained by chemical synthesis such as hydroformylation of olefins. Also, researchers have attempted to produce terminal oxidation products of medium/long-chain alkanes using biocatalytic methods because of their high regioselectivity and stereoselectivity, and mild reaction conditions. Biocatalysts may be categorized into two types, that is, whole-cell catalytic systems and isolated enzymes. The whole-cell catalytic systems have the advantage of bypassing the complicated process of expression and purification of various proteins, avoiding the effects of environmental fluctuations (such as pH) on enzyme activity, and providing spatial confinement which is required for the normal function of various alkane oxidases composed of multiple protein subunits. Nevertheless, the whole-cell catalytic systems suffer from problems of product overoxidation, the need of adding inducers to systems with inducible enzyme expression, and poor regulation of such systems.

There are microorganisms capable of metabolizing alkanes, including bacteria and fungi, whose first step in aerobic alkane decomposition is terminal oxidation of alkanes, which is catalyzed by alkane monooxygenases. There are various alkane monooxygenases, including methane monooxygenase (MMO), butane monooxygenase (BMO), alkane hydroxylase (AlkB), AlkB-like monooxygenase, members of the cytochrome P450 (CYP) family such as CYP52 and CYP153, and long-chain alkane monooxygenase (LadA). Among these, AlkB, CYP52, and CYP153 are widely distributed and extensively studied.

AlkB-like monooxygenases are membrane integrated non-heme diiron monooxygenases. In an oxidation-reduction (redox) reaction, AlkB requires redox partner proteins, including rubredoxin and rubredoxin reductase as electron donors, and it is sometimes fused with these redox partner proteins. The AlkB system encoded in the OCT plasmid of *Pseudomonas putida* GPo1 is the most thoroughly studied alkane oxidation system, and it has been used in production of octanol and dodecanol. However, the AlkB system exhibits overoxidation activity and is susceptible to product inhibition.

Members of the CYP52 protein family are membrane-bound eukaryotic class II cytochrome P450s distributed amongst many fungi, such as *Candida tropicalis*. CYP52 ω-hydroxylates alkanes and fatty acids, and can further oxidize aliphatic alcohols to aldehydes or acids. However, the CYP52 system has overoxidation activity.

Members of the CYP153 protein family are prokaryotic soluble cytochrome P450s, most of which belong to the three-component class I CYPs, consisting of a ferredoxin, a ferredoxin reductase, and a cytochrome P450. Alternatively, bacteria of the genus *Gordonia* possess a CYP153-PFOR fusion protein (PFOR is abbreviated from phthalate family oxygenase reductase). The CYP153A has less over oxidation activity and is flexible in changing redox partner proteins. Besides, it has been shown to have co-hydroxylation activity. For example, the CYP153A of *Acinetobacter* sp. OC4 can produce α, ω-alkanediol. However, one previous study has found that the redox partner proteins of the CYP153A from *Marinobacter aquaeoli* VT8 cannot sustain the activity of this CYP153A (see Scheps et al., MicrobBiotechnol. 2013 November; 6(6):694-707).

Moreover, the currently known whole-cell catalytic systems utilizing CYP153A are inducible enzyme expression systems that require the addition of inducers, and are operated using a two-step resting cell culture which separates protein expression from biotransformation. When biocatalytic methods are performed with said system, bacteria are first cultured in a suitable medium which facilitates their growth and induces enzyme expression, and then collected and transferred to another medium for biotransformation. Since said system requires the addition of an inducer such as isopropyl β-D-1-thiogalactopyranoside (IPTG) or dicyclopropylketone (DCPK) to induce the protein expression of CYP153A, there is concern about increased production costs, incomplete regulation of CYP153A protein expression, and the need to change medium. In order to simplify the aforementioned biotransformation process, it is of necessity to develop a whole-cell catalytic system that can be operated using a single-step growing cell culture and that can undergo medium/long-chain alkane-induced medium/long-chain alkane oxidation without the need of additional inducers for cytochrome expression and a change of medium.

SUMMARY OF THE INVENTION

As a result, the present invention provides a method of activating gene expression, including the step of contacting a recombinant microbial cell with a medium-chain or long-chain alkane or a medium-chain or long-chain fatty acid methyl ester, wherein the recombinant microbial cell expresses a protein having 90% or more sequence identity to SEQ ID NO:45 and includes a gene whose expression is to be activated.

In one embodiment of the present invention, the medium-chain or long-chain alkane is a straight-chain alkane having a carbon chain length of C8 or greater; the medium-chain or long-chain fatty acid methyl ester is a straight-chain saturated fatty acid methyl ester having a carbon chain length of C8 or greater, such as methyl laurate; and the gene whose expression is to be activated encodes a cytochrome P450.

In another aspect, the present invention provides a whole-cell catalytic system regulated by a medium-chain or long-chain alkane or a medium-chain or long-chain fatty acid methyl ester, including a recombinant microbial cell expressing a protein having 90% or more sequence identity to SEQ ID NO:45 and an alkane monooxygenase.

In one embodiment of the present invention, the alkane monooxygenase is a cytochrome P450, for example, the cytochrome P450 consisting of a protein of cytochrome P450 153A family (CYP153A), a ferredoxin, and a ferredoxin reductase. The cytochrome P450 may be derived from *Marinobacter aquaeoli* VT8. In another embodiment of the present invention, the aforementioned recombinant microbial cell of the whole-cell catalytic system further expresses an alkane transporter. The alkane transporter refers to a protein that promotes alkane transport from the environment to bacterial or fungal cells, such as the AlkL protein derived from *Pseudomonas putida*.

In still another aspect, the present invention provides a method of preparing a medium-chain or long-chain alkane terminal oxidation product, including the steps of: (a) providing a recombinant microorganism, including a first gene encoding an alkane monooxygenase, and a second gene encoding a protein having 90% or more sequence identity to SEQ ID NO:45; (b) incubating the recombinant microorganism in a culture medium containing a carbon source; and (c) adding a medium-chain or long-chain alkane or a medium-chain or long-chain fatty acid methyl ester to the culture medium for a predetermined period of time to obtain the medium-chain or long-chain alkane terminal oxidation product.

In one embodiment of the present invention, the alkane monooxygenase is a cytochrome P450, for example, the cytochrome P450 consisting of a CYP153A, a ferredoxin, and a ferredoxin reductase. The cytochrome P450 may be derived from *Marinobacter aquaeoli* VT8. In another embodiment of the present invention, the recombinant microorganism further includes a gene encoding an alkane transporter, the gene expression of which is regulated by an inducer. The alkane transporter may be the AlkL protein derived from *Pseudomonas putida*. The inducer includes a variety of small molecule compounds that can be used to regulate gene expression, such as a small-molecule sugar with a molecular weight of below 1 kDa.

In one embodiment of the present invention, the medium-chain or long-chain alkane is a straight-chain alkane having a carbon chain length of C8 or greater; the medium-chain or long-chain fatty acid methyl ester is a straight-chain saturated fatty acid methyl ester having a carbon chain length of C8 or greater, such as methyl laurate; and the medium-chain or long-chain alkane terminal oxidation product is an alkanol, an alkanediol, an alkanoic acid, an alkane dioic acid, a dicarboxylic acid methyl ester, an alcohol acid, or an alcohol amine having a carbon chain length of C8 or greater.

The present invention demonstrates that the AlkR protein, which is encoded by the nucleotide sequence of SEQ ID NO:1 and has the amino acid sequence of SEQ ID NO:45, activates the expression of a gene upon induction with a medium-chain or long-chain alkane or a medium-chain or long-chain fatty acid methyl ester. Therefore, by using genetic engineering techniques, a nucleotide sequence having 90% or more sequence identity to SEQ ID NO: 1 may be applied to construct a recombinant microorganism capable of sensing medium-chain or long-chain alkanes or medium-chain or long-chain fatty acid methyl esters, or to construct a recombinant microorganism that performs biotransformation under the regulation of medium-chain or long-chain alkanes or medium-chain or long-chain fatty acid methyl esters. Accordingly, the present invention provides a whole-cell catalytic system regulated by medium-chain or long-chain alkanes or medium-chain or long-chain fatty acid methyl esters, and also provides a method of preparing medium-chain or long-chain alkane terminal oxidation products using this system. The preparation method of the present invention utilizes the medium-chain or long-chain alkanes or medium-chain or the long-chain fatty acid methyl esters as both an inducer and a reactant in the production of the medium-chain or long-chain alkane terminal oxidation products, and the process of which is carried out with growing cell cultures. Thus, without the need to additionally supply the conventional inducers such as IPTG and DCPK and to change the culture medium, medium-chain or long-chain alkanes or medium-chain or the long-chain fatty acid methyl esters can be easily converted to medium-chain or long-chain alkane terminal oxidation products. In addition, when the whole-cell catalytic system of the present invention is employed selectively with an appropriate alkane oxidation system, such as the reconstructed CYP153A operon of the *Marinobacter aquaeoli* VT8, the resulting biotransformation owns the advantages of finely regulated expression of CYP153A, less over oxidation of the products, and no product inhibition. Furthermore, since the preparation method of the present invention utilizes compounds directly obtained from plant materials, for example, using methyl laurate obtained from palm oil as the starting material for biotransformation, it is an environmentally friendly process that makes full use of natural resources.

The present invention is further described in the following examples, in reference to the accompanying drawings. It should be understood that the examples given below do not limit the scope of the invention, and that modifications can be made without departing from the scope of the appended claims.

DETAILED DESCRIPTION OF THE PREFERRED EMBODIMENT

Figure 1:
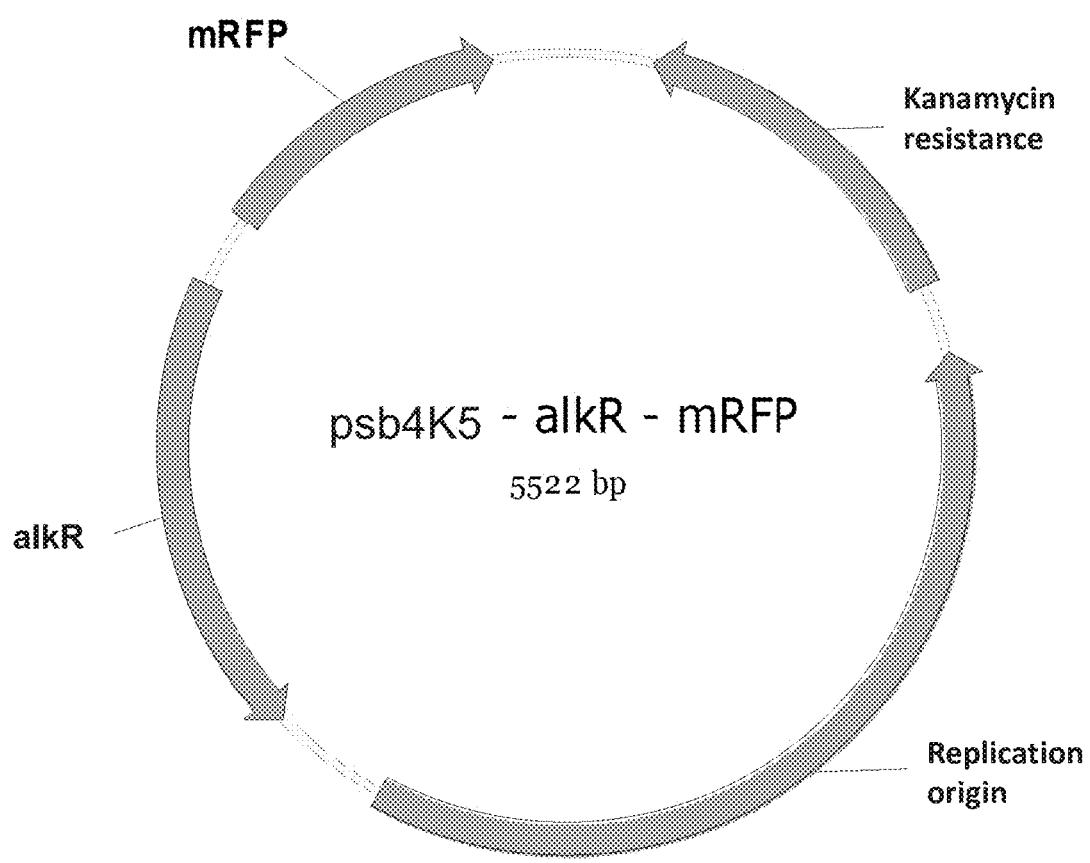
FIG. 1 shows the schematic diagram of the psb4K5-alkR-mRFP plasmid carried by a recombinant microorganism according to one embodiment of the present invention.

The present invention provides a method of activating gene expression by using a protein having 90% or more sequence identity to SEQ ID NO:45, which is encoded by the nucleotide sequence of SEQ ID NO: 1. A nucleic acid fragment having the nucleotide sequence of SEQ ID NO:1 is isolated from CYP153A operon of *M. aquaeoli* VT8, and it encodes a protein capable of sensing the presence of a medium-chain or long-chain alkane or a medium-chain or long-chain fatty acid methyl ester and activating gene expression. Therefore, this protein is identified as an alkane response regulator and herein referred to as AlkR protein. The AlkR protein has four regions of amino acids that are important for its function, namely, amino acid residues 80-93 (GLRLGKRMTPATHG, SEQ ID NO:2), 194-210 (LSGQIHFDCSQLKLSLP, SEQ ID NO:3), 278-291 (TLARKLNHEGSSFR, SEQ ID NO:4), and 316-335 (IAALMNYHDSANFRRAFKRW, SEQ ID NO:5). Based on the characteristics of the AlkR protein, the present invention also provides a whole-cell catalytic system regulated by a medium-chain or long-chain alkane or a medium-chain or long-chain fatty acid methyl ester. The system includes a recombinant microbial cell expressing a protein having 90% or more sequence identity to SEQ ID NO:45 and an alkane monooxygenase. Given that *E. coli* is advantageous in having low overoxidation activity, recombinant *E. coli* cells including the reconstructed CYP153A operon of *M. aquaeoli* VT8 are shown in the following examples to exemplify the whole-cell catalytic system of the present invention and to demonstrate the ability of such system to express a functional cytochrome P450 upon induction with medium-chain or long-chain alkanes or medium-chain or long-chain fatty acid methyl esters. The present invention also provides method of preparing a medium-chain or long-chain alkane terminal oxidation product using the whole-cell catalytic system. For example, the method includes incubating the aforementioned recombinant *E. coli* containing the CYP153A operon or a recombinant *P. putida* GPo1, each of which is allowed to undergo alkane oxidation after addition of medium-chain or long-chain alkanes or medium-chain or long-chain fatty acid methyl esters and to produce medium-chain or long-chain alkane terminal oxidation products.

Definition

Numerical quantities provided herein are approximated, experimental values that may vary within 20 percent, preferably within 10 percent, and most preferably within 5 percent. Thus, the terms "about" and "approximately" refer to within 20 percent, preferably within 10 percent, and most preferably within 5 percent of a given value or range.

As used herein, the expression "a protein having 90% or more sequence identity to SEQ ID NO:45" refers to a protein having 90% or more sequence similarity to the amino acid sequence of SEQ ID NO:45. The protein includes at least the four amino acid sequences of SEQ ID NO:2, SEQ ID NO:3, SEQ ID NO:4, and SEQ ID NO:5, and also has the function of the AlkR protein. The function of the AlkR protein can be assayed according to experimental procedures described therein.

As used herein, the term "medium-chain alkane" refers to an alkane having a carbon chain length between C8 and C12; and the term "long-chain alkane" refers to an alkane having a carbon chain length greater than C12.

As used herein, the term "medium-chain fatty acid methyl ester" is a fatty acid methyl ester (FAME) having a carbon chain length between C8 and C12, such as methyl laurate (also known as methyl dodecanoate or lauric acid methyl ester); and the term "long-chain fatty acid methyl ester" is a fatty acid methyl ester having a carbon chain length greater than C12.

As used herein, the term "medium-chain or long-chain alkane terminal oxidation product" refers to a compound that is formed by terminal oxidation of the medium-chain or long-chain alkane or the medium-chain or long-chain FAME mentioned above, and that has one or two hydroxyl groups, one or two carboxyl groups, both a hydroxyl group and a carboxyl group, or both a carboxyl group and an amine group at one or two ends of the carbon chain. Thus, the medium-chain or long-chain alkane terminal oxidation products include FAME terminal oxidation products. Said compound is an alkanol, an alkanediol, an alkanoic acid, an alkane dioic acid, a dicarboxylic acid methyl ester, an alcohol acid (also termed omega hydroxy acid), or an alcohol amine having a carbon chain length of C8 or greater.

As used herein, the term "recombinant microorganism" or "recombinant microbial cell" refers to a microorganism engineered by general genetic engineering techniques to include a deoxyribonucleic acid (DNA) that is not originally possessed by the microorganism. The recombinant microorganism includes a recombinant bacterium and a recombinant fungus.

As used herein, the term "CYP153A operon" of *M. aquaeoli* VT8 includes a gene encoding the AlkR protein, a gene encoding a CYP153A, a gene encoding a ferredoxin (abbreviated as Fdx), and a gene encoding a ferredoxin reductase (abbreviated as FdR). Each of the genes has the nucleotide sequence of SEQ ID NO:1, SEQ ID NO:6, SEQ ID NO:7, and SEQ ID NO:8, respectively.

As used herein, the expression "a predetermined period of time" refers to a period of time that is required to obtain the medium-chain or long-chain alkane terminal oxidation product.

Materials and Methods
Bacteria Culture

Bacterial strains used in the following examples include *Marinobacter aquaeoli* VT8 (*M. aquaeoli* VT8; ATCC 700491) and *Pseudomonas putida* GPo1 (*P. putida* GPo1; ATCC 29347) purchased from the American Type Culture Collection (ATCC, Manassas, Va., USA), and *E. coli* JM109 purchased from Invitrogen (USA). *M. aquaeoli* VT8 was cultured in Halomonas medium (50.0 g/L sodium chloride, 7.5 g/L casein amino acids and vitamins, 5.0 g/L proteose peptone No. 3 (BD211693), 1.0 g/L yeast extract, 3.0 g/L trisodium citrate, 20.0 g/L magnesium sulfate heptahydrate, 0.5 g/L dipotassium hydrogen phosphate, 0.05 g/L ammonium ferrous sulfate, pH 7.3). *E. coli* JM109 was cultured in Lysogeny broth medium (LB medium). Unless otherwise specified, *M. aquaeoli* VT8 and *P. putida* GPo1 were cultured at 30° C. with agitation at 150 rpm, and *E. coli* JM109 was cultured at 37° C. The aforementioned medium may be supplemented with 50 mg/L antibiotics if needed.

Terrific broth medium (TB medium; 12 g/L tryptone, 24 g/L yeast extract, 9.4 g/L dipotassium hydrogen phosphate, 2.2 g/L potassium dihydrogen phosphate, pH 7.2) was used to prepare the medium-chain or long-chain alkane terminal oxidation products via biotransformation. The medium was supplemented with a carbon source, such as glucose and glycerol.

Chromosomal DNA Extraction and DNA Manipulation

Chromosomal DNA of *M. aquaeoli* VT8 and *E. coli* JM109 was isolated using Wizard® Genomic DNA purification kit (Promega). Unless otherwise specified, all plasmids digested with restriction enzymes were dephosphorylated with alkaline phosphotase. DNA fragments were amplified by polymerase chain reaction (PCR) using primers.

Construction of a Reporter Plasmid Including an alkR Gene

The DNA fragment BioBrick BBa-J04450, which encodes the monomeric red fluorescence protein (mRFP), was used as a template for PCR amplification with a forward primer containing a StuI cleavage site and a reverse primer containing a KpnI cleavage site. The forward primer had the sequence 5'-GTTTCTTCTAGAGGCCTAAA GAGGAGAAATACTAGATGGCTTC-3' (SEQ ID NO:9), and the reverse primer had the sequence 5'-GTTTCTGGTACCATTACCGCCTTTGAGTGAGC-3' (SEQ ID NO:10). The amplified DNA fragment was digested with the restriction enzymes XbaI and PstI and cloned into a low copy vector psb4K5 (pSB4K5-I52002; BioBrick), which carries a kanamycin resistance gene, to form a plasmid psb4K5-StuI-mRFP. Also, a 1238 bp DNA fragment containing the putative alkR gene (SEQ ID NO:1) and its promoter was PCR amplified from the genomic DNA of *M. aquaeoli* VT8 using a forward primer 5'-CCTGCACTGGCTCCCCAAG-3' (SEQ ID NO:11) and a reverse primer 5'-CCCGGGACCAGCATTGATGATTGACAG-3' (SEQ ID NO:12). This amplified DNA fragment was phosphorylated by T4 polynucleotide kinase and ligated to the XbaI and PstI-digested psb4K5-StuI-mRFP plasmid to form a psb4K5-alkR-mRFP plasmid as shown in FIG. 1, which is a reporter plasmid including the alkR gene.

Alkane Induction Assay

*E. coli* JM109 carrying the psb4K5-alkR-mRFP plasmid was cultured overnight at 37° C. and 125-150 rpm in 3 mL of LB medium containing 50 μg/mL kanamycin. The overnight culture was diluted 1000-fold in LB medium in a 100 mL Hinton's flask and cultured at 37° C. To induce the expression of red fluorescent protein, 1% (v/v) of the various indicated hydrocarbons was added to the culture when the absorbance at 600 nm (O.D.600) reached about 0.6. At 0, 3, 6, 9, and 12 hours after the induction, 500 μL of the abovementioned bacterial culture was collected and centrifuged to obtain a cell pellet, which was washed twice and resuspended with phosphate buffer saline (PBS). Flow cytometry (BD FACSCanto II) was used to measure the mean fluorescence intensity of the cells and the distribution of cells with different fluorescence intensities (an excitation wavelength at 532 nm and an emission wavelength at 588 nm). For the *E. coli* JM109 that additionally carrying an expression vector of an alkane transporter, rhamnose was first added to the bacterial culture at an O.D.600 of about 0.6, and 1% (v/v) of the various indicated hydrocarbons was added three hours thereafter.

Reconstruction of the CYP153A Operon of *M. aquaeoli* VT8

Figure 2:
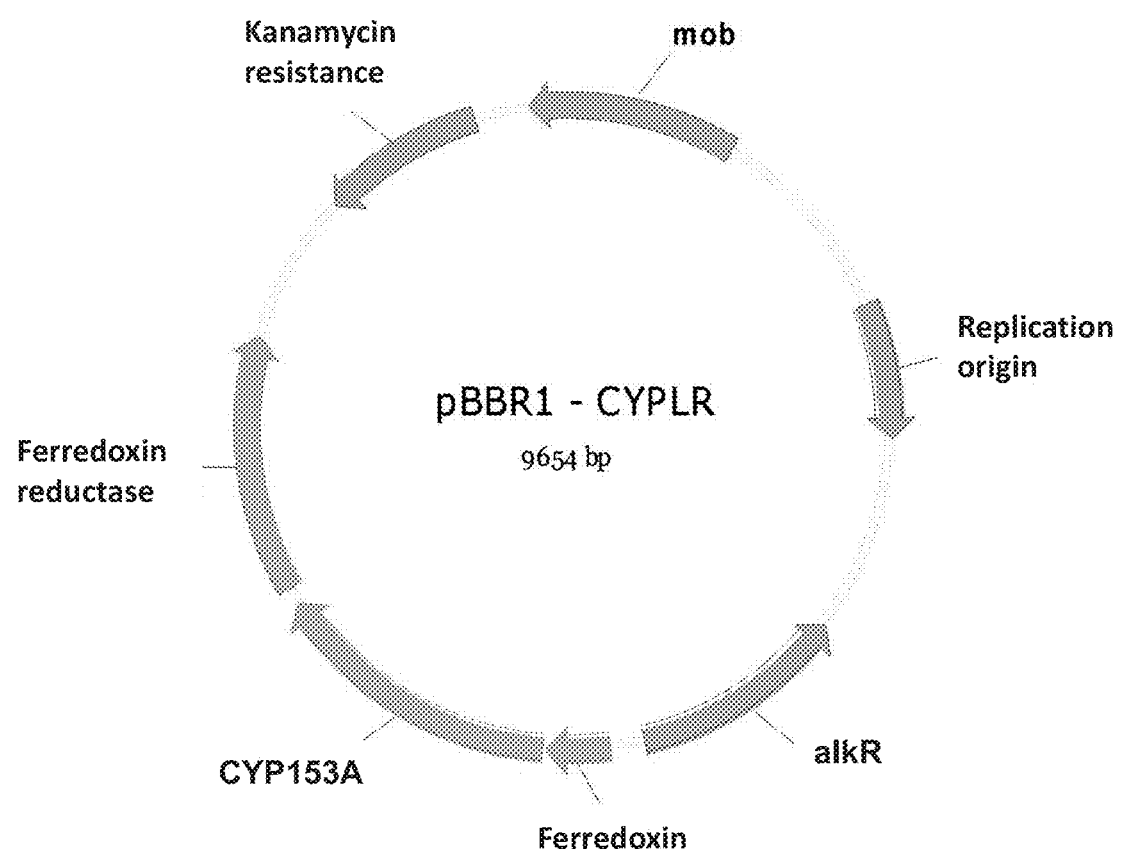
FIG. 2 shows the schematic diagram of the pBBR1-CYPLR plasmid carried by a recombinant microorganism according one embodiment of the present invention.

The CYP153A operon in the commercially available *M. aquaeoli* VT8 is functionally defective as including a transposon at a position corresponding to the amino terminus (N-terminus) of the ferredoxin. Thus, the CYP153A operon is reconstructed in the present invention using the homologous DNA sequence form *Marinobacter salarius* R9SW1 (NZ_CP007152.1) as reference. First, a 1286 bp DNA fragment encoding the putative AlkR protein and the N-terminus of ferredoxin was PCR amplified with a forward primer 5'-GTTTCTTCTAGAGCACTGGCTCCCCAAG-3' (SEQ ID NO:13) and a reverse primer 5'-GATATCATGTTCGATAAACGTAACTTTG-3' (SEQ ID NO:14). This PCR was performed where denaturation (98° C.) for 10 seconds followed by annealing (55° C.) for 20 seconds and extension (72° C.) for 45 seconds was repeated 30 cycles. The amplified PCR product, after digested with restriction enzymes, were ligated to an XbaI and StuI-digested pBBR1-rha vector having the framework of the Gram-negative plasmid PBBR1-MCS-2 to form a pBBR1-CYPL plasmid. Next, a 3045 bp DNA fragment downstream of the transposon was PCR amplified with a forward primer 5'-CAAACTGAACATGTCGCAGAATTCAAAGC-3' (SEQ ID NO:15) and a reverse primer 5'-TTATCAACTCTGGAGCCTTCCGT-3' (SEQ ID NO:16). The amplified DNA fragment was phosphorylated by T4 polynucleotide kinase and ligated to the pBBR1-CYPL plasmid, which had been treated with the restriction enzyme EcoRV and the alkaline phosphatase CIP, to form a pBBR1-CYPLR plasmid as shown in FIG. 2, which is a plasmid including the reconstructed CYP153A operon. This plasmid was verified to contain a ribosome binding site (RBS) for the ferredoxin gene and a start codon and was able to be used as a protein expression vector. A pBBR1-alkR plasmid including only the alkR gene, which was used as control, was also prepared as follows. A 1244 bp DNA fragment including the alkR gene and its promoter was PCR amplified with a forward primer having the nucleotide sequence of SEQ ID NO:13 and a reverse primer 5'-CCTACCAGCATTGATGATTGACAG-3' (SEQ ID NO:17), and the amplified DNA fragment digested with restriction enzymes was ligated to the XbaI and StuI-digested pBBR1-rha vector.

Expression of CYP153A

*E. coli* JM109 carrying the pBBR1-CYPLR plasmid or the pBBR1-alkR plasmid was overnight cultured at 37° C. and 125-150 rpm in 3 mL of LB medium containing 50 μg/mL kanamycin. The overnight culture was diluted 1000-fold in 3 mL of LB medium containing 50 μg/mL kanamycin and cultured at 37° C. 1% (v/v) methyl laurate was added to the culture at an O.D.600 of about 0.6 and a further incubation at 30° C. was carried out for 12 hours. The cell pellet obtained by centrifuging the abovementioned bacterial culture was washed and resuspended with PBS, and then subjected to protein expression analysis by sodium dodecyl sulfate polyacrylamide gel electrophoresis (SDS-PAGE) or carbon monoxide (CO) difference spectroscopy.

Sodium Dodecyl Sulfate Polyacrylamide Gel Electrophoresis (SDS-PAGE)

Samples of bacterial cells were mixed with sample buffer (50 mM Tris-HCl, pH 6.8, 100 mM dithiothreitol (DTT), 2% SDS, 0.1% bromophenol blue, 10% glycerol) and boiled for 10 minutes. Also, electrophoresis gels including a 12% separating gel (2.5 mL of 1 M Tris, pH 8.8, 3.3 mL deionized water, 4 mL of 30% acrylamide mix, 0.1 mL of 10% SDS, 0.1 mL of 10% ammonium persulfate (APS), 0.01 mL TEMED) and a 5% stacking gel (0.63 mL of 1 M Tris, pH 6.8, 3.4 mL deionized water, 0.83 mL of 30% acrylamide mix, 0.05 mL of 10% SDS, 0.05 mL of 10% APS, 0.005 mL TEMED) were casted. Electrophoresis was performed at 80V for stacking and at 150V for separating. Gels were then stained in coomassie blue staining solution (0.1% coomassie R250, 10% acetic acid, and 50% methanol) for 1 hour and destained with destaining solution (10% acetic acid and 50% methanol).

CO Difference Spectroscopy

Bacterial culture was chilled on ice for 10 minutes and centrifuged at 3000 g for 5 minutes to obtain a cell pellet, which was washed twice with PBS and resuspended in P450 spectrum buffer (100 mM Tris-HCl, 20% (v/v) glycerol, 1 mM ethylenediaminetetraacetic acid (EDTA), pH 7.4) to form a bacterial sample. A few grams of sodium dithionite was then added to and mixed with the sample by inversion. After reaction for 10 minutes, a baseline was set by scanning the sample with an ultraviolet-visible spectrophotometer (Thermo Genesys 10) from 400 nm to 500 nm. Thereafter, carbon monoxide was applied to the sample for one minute at the rate of one bubble per second, and the CO-saturated sample was scanned again from 400 nm to 500 nm for an absorption spectrum.

Gas Chromatography and Gas Chromatography/Mass Chromatography (GC/MS)

The medium-chain or long-chain alkane terminal oxidation product in the sample was analyzed qualitatively and quantitatively by gas chromatography. The analysis of alkanols and alkanediols was described as follows, with 1-octanol taken as example. 10 mg of 1,8-octanediol was added as an internal standard to 10 mL of the collected bacterial culture, and the mixture was extracted twice with double volumes of ethyl acetate. The organic phase was collected, dried with rotary evaporator, and dissolved in 60 μL of methyl tert-butyl ether (MTBE), followed by the addition of 60 mL of 1% trimethylchlorosilane (TMCS) in N,O-bis-(trimethylsilyl)trifluoroacetamide (BSTFA) and incubation at 75° C. for 30 minutes for derivatization. The obtained product was analyzed for composition by Varian CP-3800 gas chromatograph equipped with a DB-5 column and a flame ionization detector (FID). For the analysis, the carrier gas was nitrogen at a flow rate of 0.8 mL/min; the injector temperature was 300° C.; the temperature of the column oven was set to 150° C. for 2 minutes and then raised to 300° C. at a rate of 20° C. per minute. Alkanoic acids, alkanedioic acids, or alcohol acids were analyzed similarly as described above. In one embodiment of the present invention, 12-hydroxydodecanoic acid was analyzed using dodecanol as the internal standard.

The medium-chain or long-chain alkane terminal oxidation product in the sample was identified by gas chromatography/mass spectrometry with Agilent 5975 GC/MS system equipped with a HP-5 ms column. For analysis, helium was used as the carrier gas; the temperatures of the injector and the detector were 250° C. and 300° C., respectively; the temperature program of the column oven was the same as described above; the ionization method was electrospray ionization at 70 eV.

Construction of Rhamnose-Inducible Alkane Transporter Expression Vectors

Figure 3:
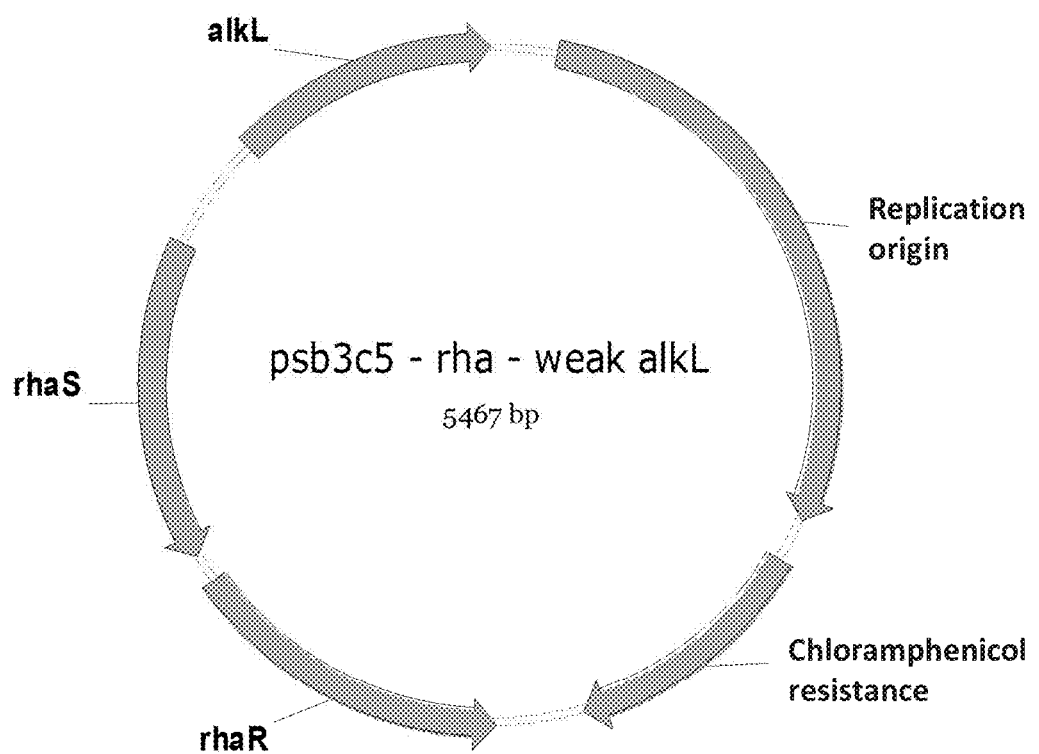
FIG. 3 shows the schematic diagram of the psb3C5-rha-weak alkL plasmid carried by a recombinant microorganism according to one embodiment of the present invention.

Construction of the rhamnose-inducible expression vector of alkane transporter is described as follows, with the alkane transporter AlkL (CAB54056.1) of *P. putida* GPol taken as example. First, the DNA fragment including the rhamnose promoter RhaP$_{BAD}$ and two genes encoding the rhamnose regulatory proteins RhaR and RhaS was PCR amplified from the *E. coli* JM109 genomic DNA using a forward primer 5'-GTTTCTTCTAGAGTTAATCTTTCTGCAATT-GAGATG-3' (SEQ ID NO:18) and a reverse primer 5'-GTTTCTCTGCAGCGGCCGCTAGGCC-TATACGACCAGTCTAAA AAGCGC-3' (SEQ ID NO:19). The amplified PCR product was digested with restriction enzymes and ligated to the XbaI and StuI-digested psb3C5 vector (pSB3C5-I52001; BioBrick) to form a psb3C5-rha vector. Next, the alkL gene was PCR amplified with a forward primer 5'-TCACACAGGACTACTAGAT-GAGTTTTTCTAATTATAAAGTAA TCGCG-3' (SEQ ID NO:20) including a weak ribosome binding site (weak RBS) and a reverse primer 5'-TTAGAAAACATATGACGCAC-CAA-3' (SEQ ID NO: 21). The amplified PCR product was phosphorylated by T4 polynucleotide kinase and ligated to the psb3C5-rha vector that had been digested with the restriction enzyme PstI and the Klenow fragment to form a psb3C5-rha-weak AlkL plasmid as shown in FIG. 3, which is an expression vector of the AlkL protein.

Figure 4:
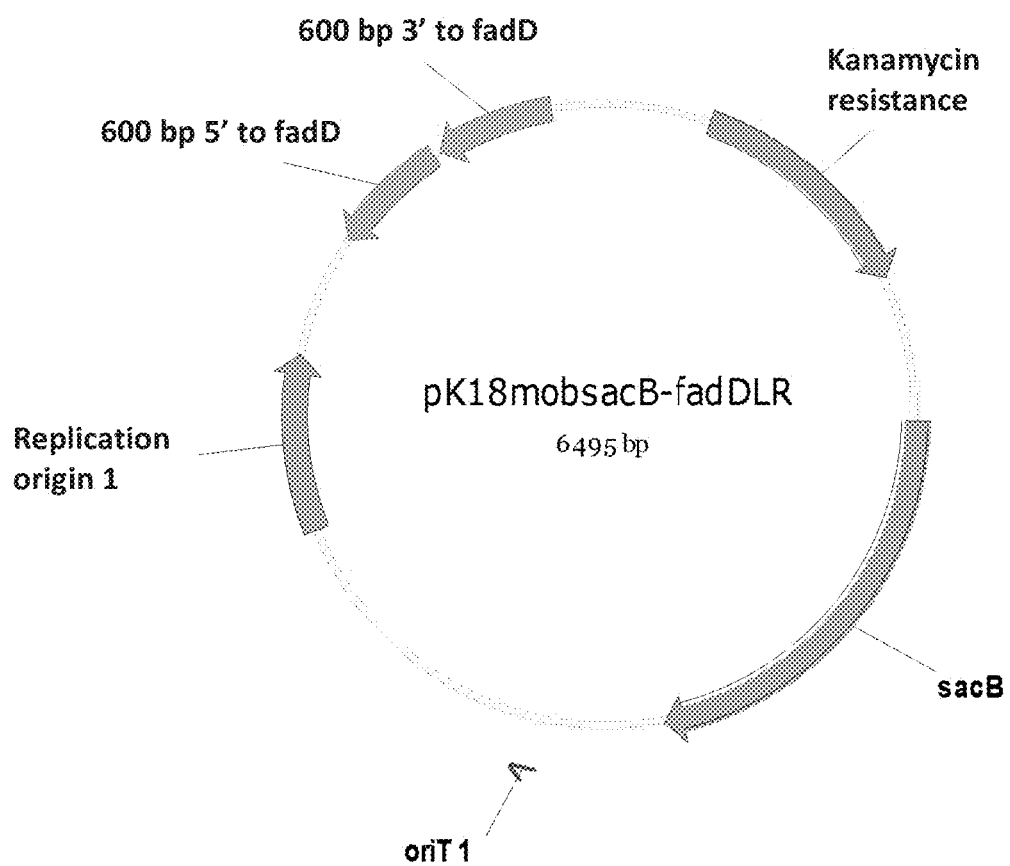
FIG. 4 shows the schematic diagram of the pK18mobsacB-fadDLR plasmid used to construct a recombinant microorganism with a interrupted β-oxidation pathway.
Figure 5:
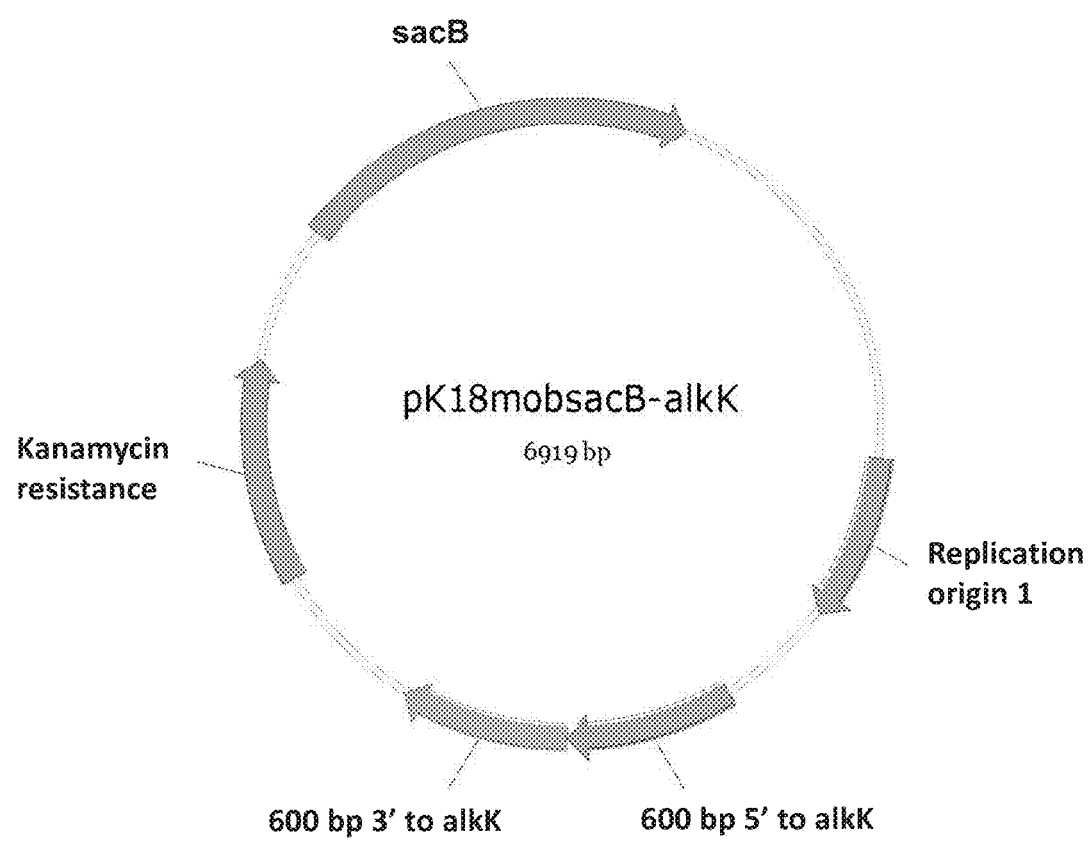
FIG. 5 shows the schematic diagram of the pK18mobsacB-alkK plasmid used to construct a recombinant microorganism in which the β-oxidation pathway is blocked.

Construction of the Recombinant *P. putida* GPol Having the Interrupted β-Oxidation Pathway and Utilizing n-Dodecane Efficiently A recombinant *P. putida* GPol was described as one example of the whole-cell catalytic system for the preparation of alkanoic acids and alkanedioic acids. In order to improve the efficiency of producing alkanoic acids and alkanedioic acids by *P. putida* GPol, the 600 bp DNA fragments flanking each of the fadD and alkK genes were PCR amplified with the primers listed in TABLE 1, and the two sets of PCR products were separately cloned into the pK18mobsacB plasmid (ATCC 87097) using the Gibson Assembly Master Mix kit (New England Biolabs) to generate the pK18mobsacB-fadDLR plasmid (FIG. 4) or the pK18mobsacB-alkK plasmid (FIG. 5). Through bi-parental mating transformation and double crossing-over homologous recombination, the aforementioned two plasmids were introduced into *P. putida* GPol, and the acs1, acs2, and alkK genes each encoding acyl-CoA synthetase, which mediates the fatty acid β-oxidation pathway, were destroyed. The genetic defects in the resulting *P. putida* GPol having the interrupted β-oxidation pathway were verified by extracting and PCR amplifying the defective acs1, acs2, and alkK genes from the genomic DNA of the *P. putida* GPol.

TABLE 1

| Target DNA | Nucleotide sequences of forward (F) and reverse (R) primers |
|---|---|
| 600 bp 5' to fadD gene | F: CGAATTCGAGCTCGGTACCCTCAGGCGATCTTCTTCAAACC (SEQ ID NO: 22)<br>R: ATGTTCGGCACTGGCTGAAGACCGGTGAC (SEQ ID NO: 23) |
| 600 bp 3' to fadD gene | F: CTTCAGCCAGTGCCGAACATGTTCAGGTAC (SEQ ID NO: 24)<br>R: GTCGACTCTAGAGGATCCCCATGCAAGCCGACTTCTGG (SEQ ID NO: 25) |
| 600 bp 5' to alkK gene | F: TCGAGCTCGGTACCCATGTTAGGTCAGATGATGC (SEQ ID NO: 26)<br>R: TCTGGAGAGCGGTGTGAATAAAGTAC (SEQ ID NO: 27) |

TABLE 1-continued

| Target DNA | Nucleotide sequences of forward (F) and reverse (R) primers |
|---|---|
| 600 bp 3' to alkK gene | F: CACACCGCTCTCCAGATGAAAAGCTTTC (SEQ ID NO: 28)<br>R: CTCTAGAGGATCCCCTTATTCACAGACAGAAGAACTAC (SEQ ID NO: 29) |

Figure 6:
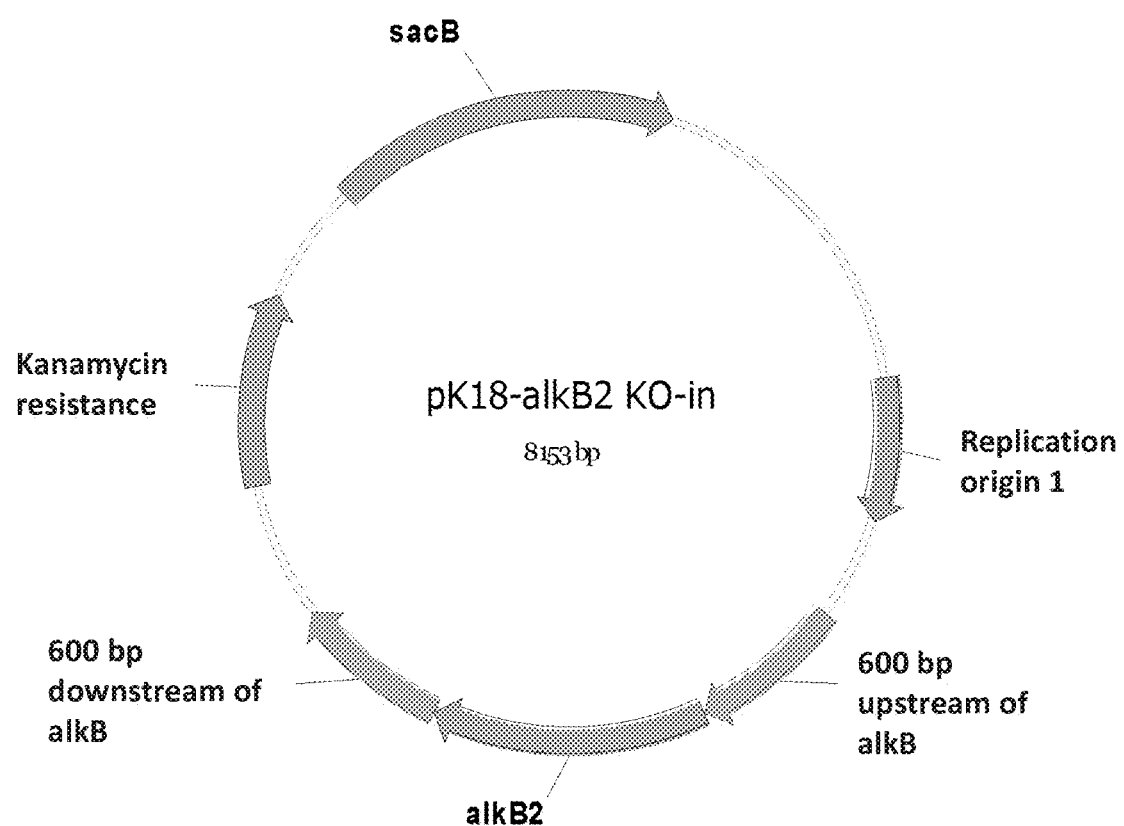
FIG. 6 shows the schematic diagram of the pK18-alkB2 KO-in plasmid used to construct a recombinant *Pseudomonas putida* GPo1; the plasmid was used for the expression of the alkane hydroxylase AlkB2 system of *Pseudomonas aeruginosa* PAO1.
Figure 7:
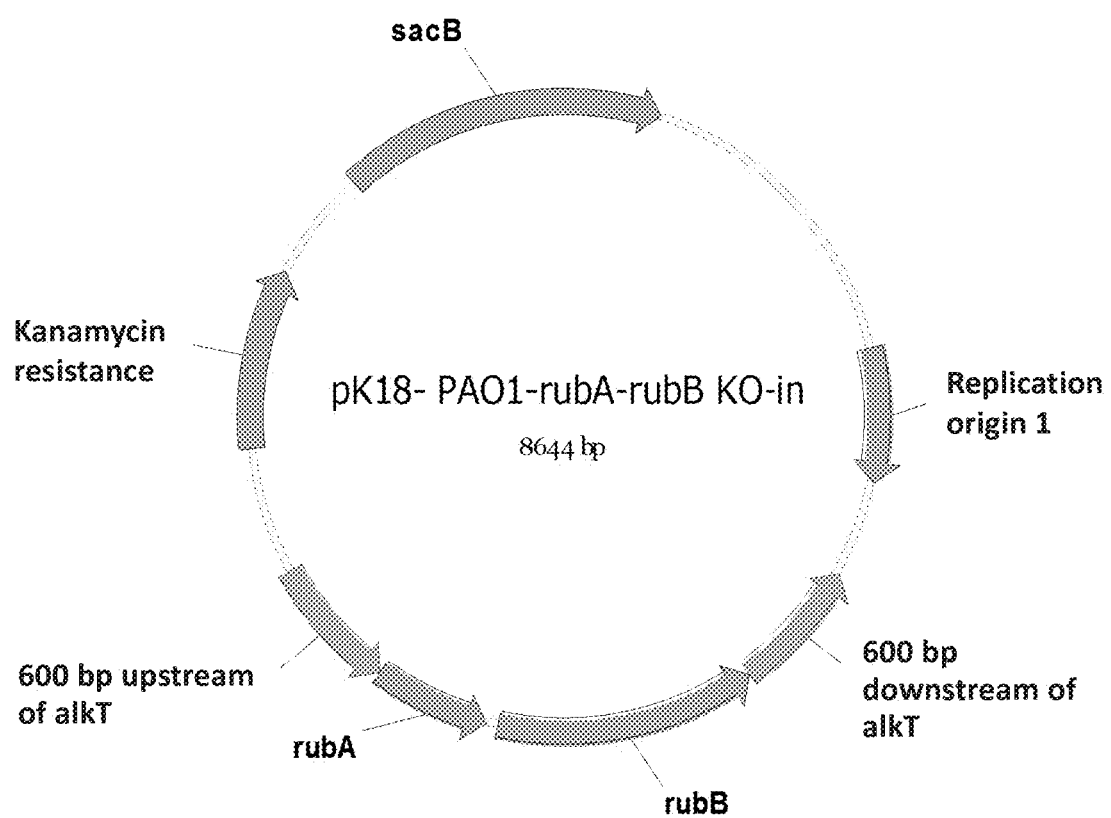
FIG. 7 shows the schematic diagram of the pK18-PAO1-rubA-rubB KO-in plasmid used to construct the recombinant *P. putida* GPo1; the plasmid was used for the expression of the alkane hydroxylase AlkB2 system of *P. aeruginosa* PAO1.

In addition, in order to enhance the terminal oxidation of n-dodecane, the genes encoding the alkane hydroxylase AlkB2, the rubredoxin RubA, and the rubredoxin reductase RubB in *Pseudomonas aeruginosa* PAO1 were substituted for the genes encoding the alkane hydroxylase AlkB and the rubredoxin reductase AlkT on the OCT plasmid of the *P. putida* GPo1. In brief, the alkB2 gene of *P. aeruginosa* PAO1 and the 600 bp DNA fragments upstream and downstream of the alkB gene of *P. putida* GPo1 were PCR amplified with the primers listed in TABLE 2, and the PCR products were then cloned to the pK18mobsacB plasmid to generate the pK18-alkB2 KO-in plasmid (FIG. 6); the rubA-rubB genes of *P. aeruginosa* PAO1 and the 600 bp DNA fragments upstream and downstream of the alkT gene of *P. putida* GPo1 were PCR amplified with the primers listed in TABLE 2, and the PCR products were then cloned to the pK18mobsacB plasmid to generate the pK18-PAO1-rubA-rubB KO-in plasmid (FIG. 7). Through bi-parental mating transformation and double crossing-over homologous recombination, the aforementioned two plasmids were introduced into the recombinant *P. putida* GPo1 having the interrupted β-oxidation pathway and gene substitution was completed. Successful gene substitution was verified by PCR. The alkB2, rubA, and rubB genes have the nucleotide sequences of SEQ ID NO:42, SEQ ID NO:43, and SEQ ID NO:44, respectively.

To demonstrate that the regulatory effect of AlkR protein on gene expression is induced by medium-chain or long-chain alkanes or medium-chain or long-chain fatty acid methyl esters, a gene encoding a red fluorescent protein was used as a reporter gene. First, *E. coli* JM109 was transformed with the psb4K5-alkR-mRFP plasmid shown in FIG. 1, which was a reporter plasmid including the alkR gene, the gene encoding the red fluorescent protein, and the promoter thereof. The transformed *E. coli* was then cultured in LB medium, and the expression of red fluorescent protein was induced by adding 1% (v/v) n-octane, n-decane, n-dodecane, n-tetradecane, n-hexadecane, n-octadecane, or methyl laurate to the medium at an O.D.600 of about 0.6, as described in the method for alkane induction assay. At 0, 3, 6, 9, and 12 hours after the induction, the mean fluorescence intensity and fluorescence distribution of *E. coli* cells were measured by flow cytometry. The recombinant *E. coli* untreated with any of the aforementioned alkanes was used as control.

Figure 8:
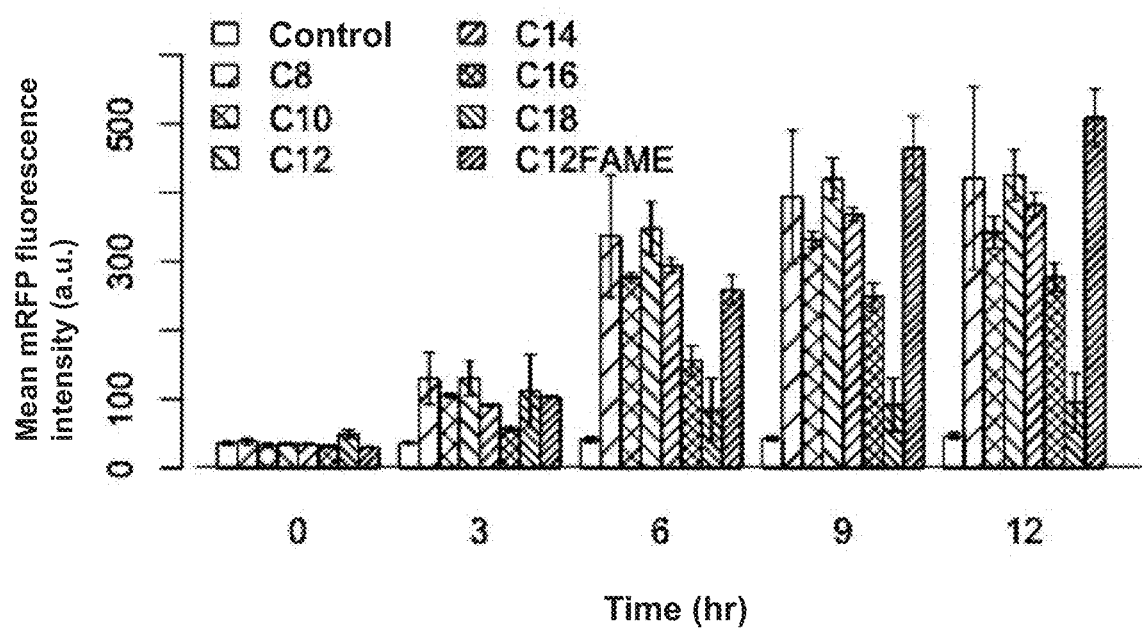
FIG. 8 shows the mean fluorescence intensity of recombinant E. coli cells carrying the psb4K5-alkR-mRFP plasmid after induction with 1% n-octane (C8), n-decane (C10), n-dodecane (C12), n-tetradecane (C14), n-hexadecane (C16), n-octadecane (C18), or methyl laurate (C12FAME)

FIG. 8 shows the red fluorescence intensity (a.u.) of the aforementioned recombinant *E. coli*. According to this figure, the straight-chain alkanes having a carbon chain length between C8 and C18 induced significantly more expression of the red fluorescent protein in the recombinant *E. coli* carrying the psb4K5-alkR-mRFP plasmid relative to the control group. In addition, methyl laurate also induced the

TABLE 2

| Target DNA | Nucleotide sequences of forward (F) and reverse (R) primers |
|---|---|
| 600 bp upstream of alkB gene | F: CGAATTCGAGCTCGGTACCCCGCTGTTGCTTGGGGCGC (SEQ ID NO: 30)<br>R: AGGCAAACATTTGGTGTTCTCCAATTTTTATTAAATTAGTCGCTACGAG (SEQ ID NO: 31) |
| 600 bp downstream of alkB gene | F: GCGCATCTGATTATGTGAGCACGCAGAG (SEQ ID NO: 32)<br>R: GTCGACTCTAGAGGATCCCCGTCAAATTGTTATTTTGCGTTG (SEQ ID NO: 33) |
| alkB2 gene | F: AGAACACCAAATGTTTGCCTCGCTTTCC (SEQ ID NO: 34)<br>R: GCTCACATAATCAGATGCGCTGGGTGTC (SEQ ID NO: 35) |
| 600 bp upstream of alkT gene | F: ACTTCTTCATAATTCTCTCTCCGGTATACTTTTC (SEQ ID NO: 36)<br>R: GTCGACTCTAGAGGATCCCCCACTAGTGCTTTCCCGAG (SEQ ID NO: 37) |
| 600 bp downstream of alkT gene | F: CGAATTCGAGCTCGGTACCCGGCGTGCACCTGGCGCTT (SEQ ID NO: 38)<br>R: CATGGCTTGACAATGATGCTCAGCCACTCGAACC (SEQ ID NO: 39) |
| rubA-rubB gene | F: AGCATCATTGTCAAGCCATGAGGCCGGG (SEQ ID NO: 40)<br>R: CGGAGAGAGAATTATGAAGAAGTGGCAATGCGTG (SEQ ID NO: 41) |

Example 1

Expression of Fluorescent Proteins in the Recombinant AlkR-Expressing Microorganism Upon Induction with Medium-Chain or Long-Chain Alkanes or Methyl Laurate expression of red fluorescent protein. The results indicate that the AlkR protein, encoded by the nucleotide sequence of SEQ ID NO: 1 and having the amino acid sequence of SEQ ID NO:45, is capable of sensing the presence of medium-chain or long-chain alkanes or medium-chain or long-chain fatty acid methyl esters and activating the expression of a gene. The results also suggest that a nucleotide sequence having 90% or more sequence identity to SEQ ID NO: 1 encodes a protein functionally identical to the AlkR protein, and that a protein having 90% or more sequence identity to SEQ ID NO:45 may function as the AlkR protein.

Figure 9A:
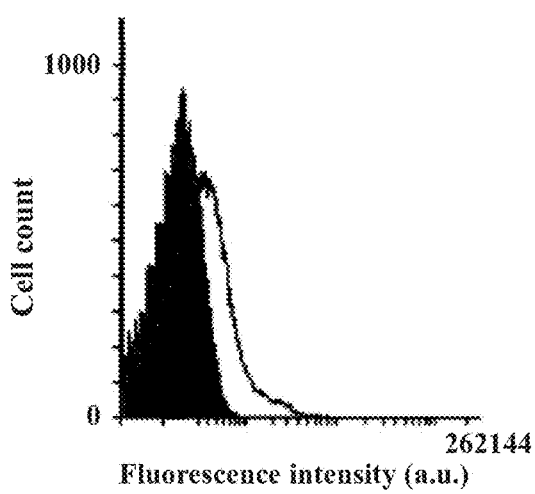
FIG. 9A shows the fluorescence distribution histograms of recombinant E. coli cells carrying the psb4K5-alkR-mRFP plasmid at 0 (black) and 6 hours (white) after induction with 1% n-octane.
Figure 9B:
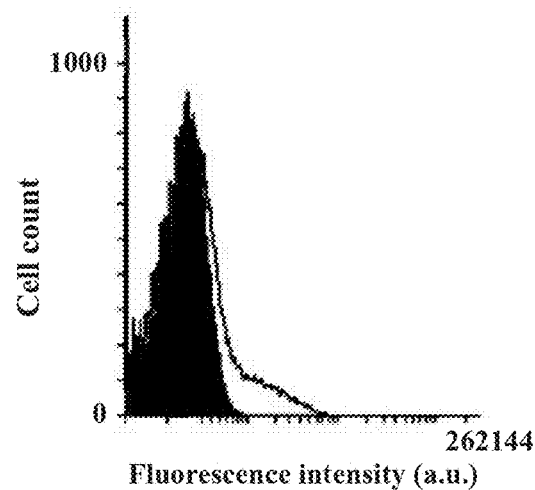
FIG. 9B shows the fluorescence distribution histograms of recombinant E. coli cells carrying the psb4K5-alkR-mRFP plasmid at 0 (black) and 6 hours (white) after induction with 1% n-decane.
Figure 9C:
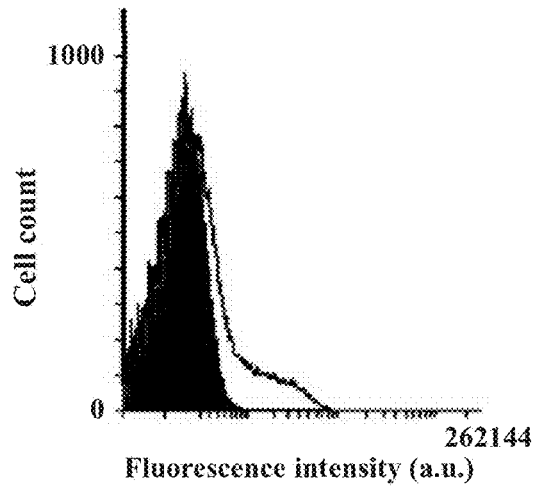
FIG. 9C shows the fluorescence distribution histograms of recombinant E. coli cells carrying the psb4K5-alkR-mRFP plasmid at 0 (black) and 6 hours (white) after induction with 1% n-dodecane.
Figure 9D:
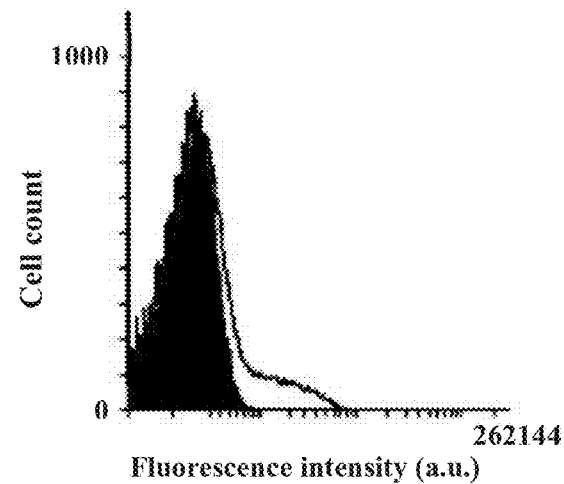
FIG. 9D shows the fluorescence distribution histograms of recombinant E. coli cells carrying the psb4K5-alkR-mRFP plasmid at 0 (black) and 6 hours (white) after induction with 1% n-tetradecane.
Figure 9E:
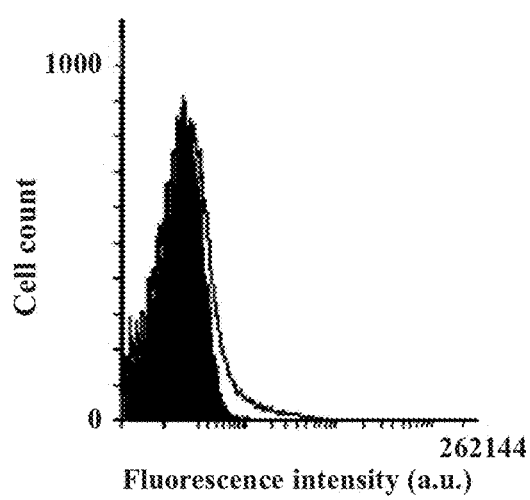
FIG. 9E shows the fluorescence distribution histograms of recombinant E. coli cells carrying the psb4K5-alkR-mRFP plasmid at 0 (black) and 6 hours (white) after induction with 1% n-hexadecane.
Figure 9F:
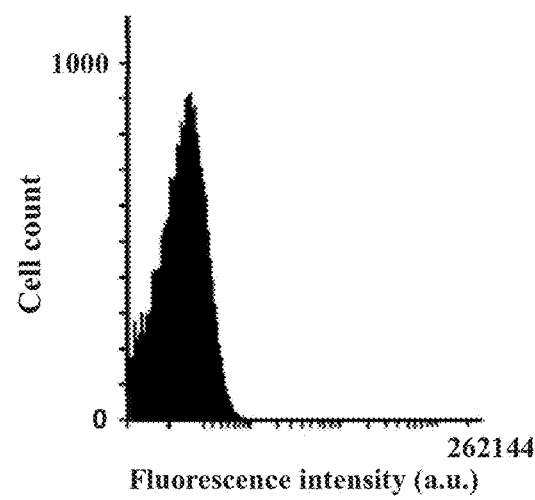
FIG. 9F shows the fluorescence distribution histograms of recombinant E. coli cells carrying the psb4K5-alkR-mRFP plasmid and untreated with any alkanes (control group) at 0 (black) and 6 hours (white)

FIGS. 9A-9E show the fluorescence distribution histograms of the aforementioned *E. coli* at 0 (black) and 6 hours (white) after induction with 1% (v/v) alkanes of various carbon chain lengths, and FIG. 9F shows the fluorescence distribution histogram of the control group. According to FIGS. 9A-9F, when the straight-chain alkanes having a carbon chain length greater than C8 were used for induction, fewer *E. coli* cells were induced to express the red fluorescent protein, and thus only peak tails were observed on the high-fluorescence intensity side of the histograms. In contrast, more *E. coli* cells were induced to express the red fluorescent protein in the presence of n-octane. This result shows that *E. coli* has lower permeability to the medium-chain and long-chain alkanes having a carbon chain length greater than C8.

Figure 10:
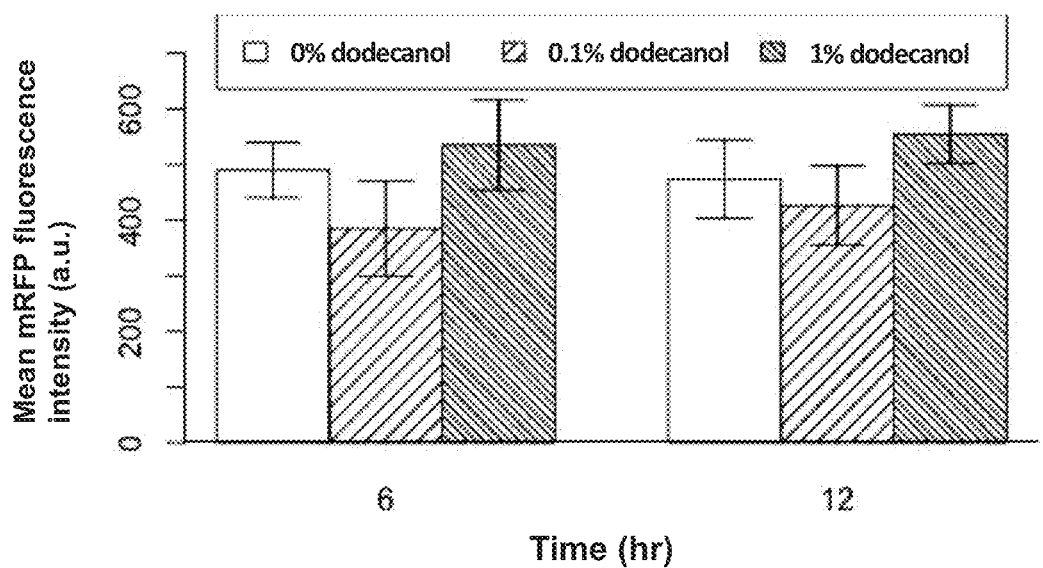
FIG. 10 shows the mean fluorescence intensity of recombinant E. coli cells carrying the psb4K5-alkR-mRFP plasmid at 6 and 12 hours after induction with 1% n-dodecane in the presence of various concentrations of 1-dodecanol.

It was also studied whether the medium-chain or long-chain alkane terminal oxidation products would inhibit the activating effect of the AlkR protein on gene expression. In the alkane induction assay using n-dodecane as the inducer, 0.1% (v/v) or 1% (v/v) 1-dodecanol was additionally added to the *E. coli* culture, and the mean fluorescence intensity of the *E. coli* cells was measured at 6 and 12 hours after the induction, with the results shown in FIG. 10. According to FIG. 10, the addition of 1-dodecanol did not inhibit the expression of red fluorescent protein, indicating that the ability of AlkR protein to activate gene expression was not inhibited by the medium-chain or long-chain alkane terminal oxidation products.

Example 2

CYP153A Expression in the Recombinant Microorganism Including the CYP153A Operon Upon Induction with Methyl Laurate It was studied whether CYP153A expression in the recombinant *E. coli* carrying the reconstructed CYP153A operon from *M. aquaeoli* VT8 would be induced by medium-chain or long-chain fatty acid methyl esters. First, *E. coli* JM109 was transformed with the pBBR1-CYPLR plasmid including the CYP153A operon, as shown in FIG. 2, or the pBBR1-alkR plasmid including only the alkR gene. The CYP153A operon includes four genes respectively encoding the AlkR protein, the CYP153A, the ferredoxin (Fdx), and the ferredoxin reductase (FdR). The transformed *E. coli* was then cultured in LB medium, and the expression of CYP153A was induced by adding 1% (v/v) methyl laurate to the medium at an O.D.600 of about 0.6. At 12 hours after the induction, the expression of CYP153A was analyzed by SDS-PAGE, and the protein molecular size and activity of the cytochrome P450 consisting of CYP153A, ferredoxin, and ferredoxin reductase were verified by carbon monoxide difference spectroscopy.

Figure 11:
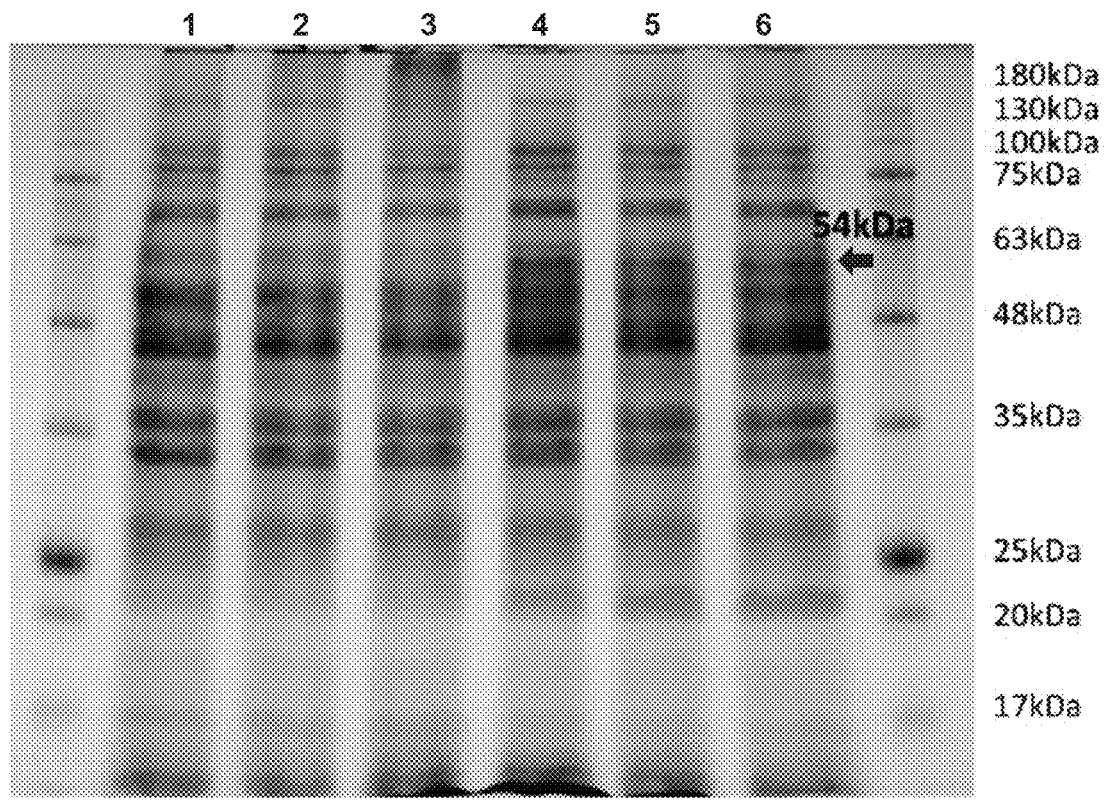
FIG. 11 shows SDS-PAGE (sodium dodecyl sulfate polyacrylamide gel electrophoresis) analysis of CYP153A expression in the recombinant E. coli carrying the pBBR1-alkR plasmid or the pBBR1-CYPLR plasmid after induction with 1% methyl laurate; gel lanes 1, 2, and 3 show triplicate samples of the recombinant E. coli with the pBBR1-alkR plasmids, and gel lanes 4, 5, 6 show triplicate samples of the recombinant E. coli with pBBR1-CYPLR plasmids.

FIG. 11 shows an image of SDS-PAGE analysis of the recombinant *E. coli*, wherein the triplicate samples in gel lanes 1, 2 and 3 were collected from the recombinant *E. coli* carrying the pBBR1-alkR plasmid, and the triplicate samples in gel lanes 4, 5 and 6 were collected from the recombinant *E. coli* carrying the pBBR1-CYPLR plasmid. According to FIG. 11, the recombinant *E. coli* carrying the pBBR1-CYPLR plasmid expressed the CYP153A with a molecular weight of approximately 54 kDa (indicated by the black arrow) upon the induction of methyl laurate. This result shows that the reconstructed CYP153A operon in the present invention functions normally, and that the recombinant microorganism including the CYP153A operon can be induced to express the CYP153A in response to the medium-chain fatty acid methyl ester such as methyl laurate.

Figure 12A:
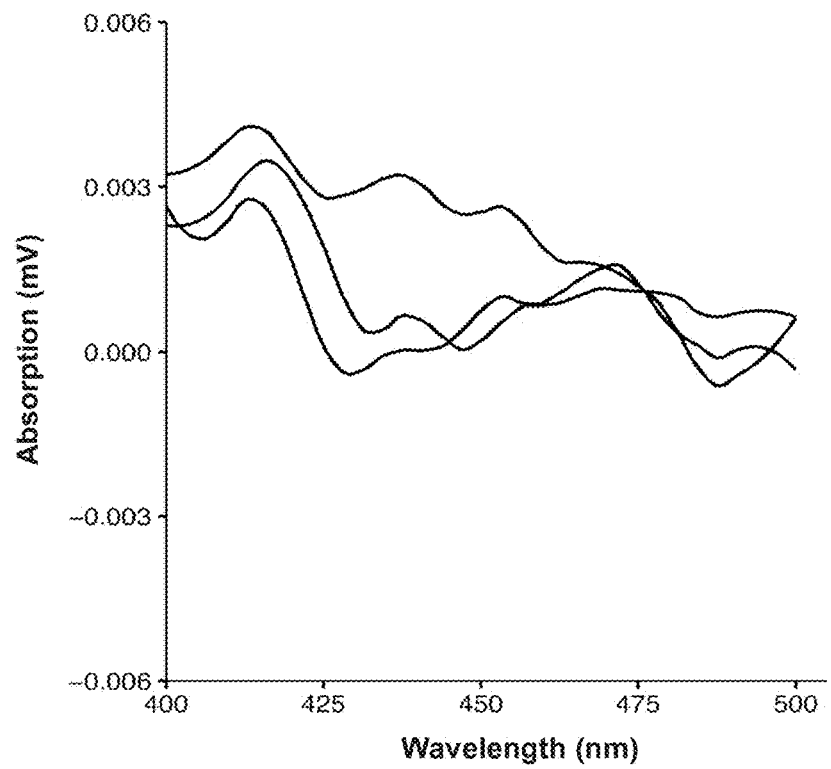
FIG. 12A shows the carbon monoxide difference spectra of the recombinant E. coli carrying the pBBR1-alkR plasmid after induction with 1% methyl laurate; the three curves are representative of triplicate samples.
Figure 12B:
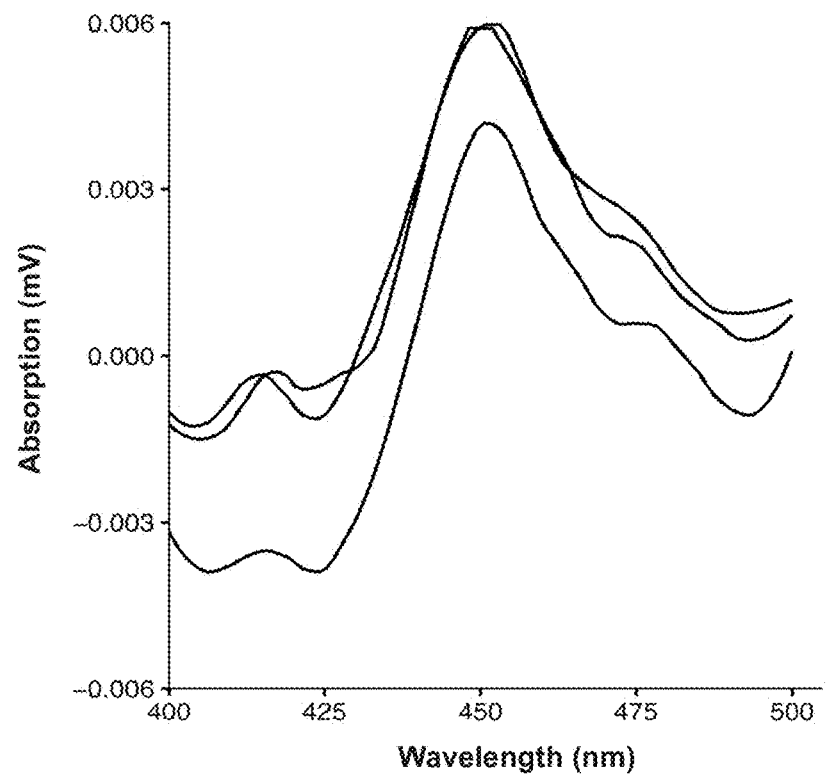
FIG. 12B shows the carbon monoxide difference spectra of the recombinant E. coli carrying the pBBR1-CYPLR plasmid after induction with 1% methyl laurate; the three curves are representative of triplicate samples.

FIGS. 12A-12B show the whole-cell carbon monoxide difference spectra (from 400 nm to 500 nm) of triplicate samples of the aforementioned two recombinant *E. coli*. A comparison of FIG. 12A and FIG. 12B shows that the recombinant *E. coli* carrying the pBBR1-CYPLR plasmid had an absorption peak at about 450 nm, indicating that the recombinant microorganism including the CYP153A operon can be induced to express the CYP153A, the ferredoxin, and the ferredoxin reductase in response to the medium-chain fatty acid methyl ester such as methyl laurate, and that the three proteins can form a correctly folded cytochrome P450.

Example 3 n-Octane-Induced 1-Octanol Production by the Recombinant Microorganism Including the CYP153A Operon It was studied whether the recombinant *E. coli* carrying the reconstructed CYP153A operon from *M. aquaeoli* VT8 would be induced to express the cytochrome P450 with oxidative activity and produce medium-chain or long-chain alkane terminal oxidation products in response to medium-chain or long-chain alkanes. According to the procedures described in Example 2, the recombinant *E. coli* carrying the pBBR1-alkR plasmid or the pBBR1-CYPLR plasmid was cultured in 10 mL of LB medium, and the expression of cytochrome P450 was induced by adding 1% (v/v) n-octane to the medium at an O.D.600 of about 0.6. At 12 hours after the induction, the production of 1-octanol in the bacterial culture was analyzed by gas chromatography.

Figure 13:
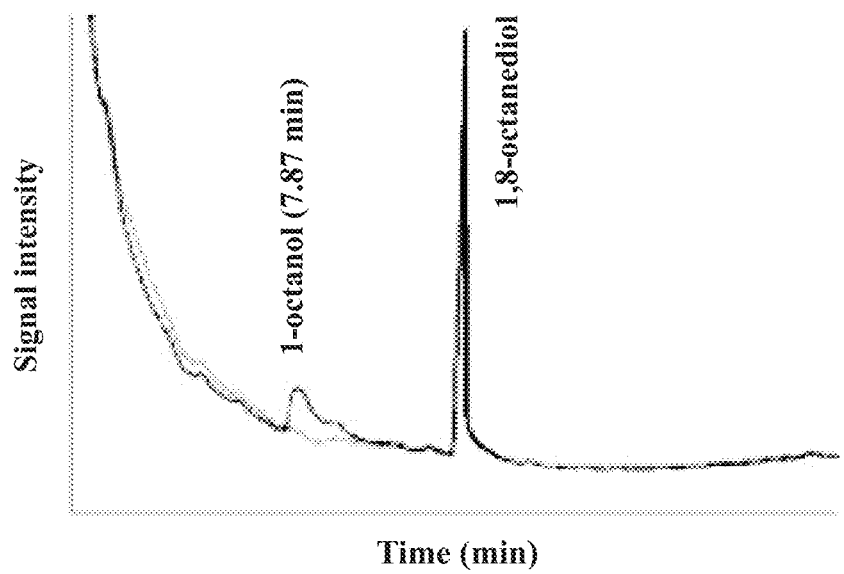
FIG. 13 shows an overlay of gas chromatograms of the recombinant E. coli carrying the pBBR1-CYPLR plasmid (dark grey curve) or the pBBR1-alkR plasmid (light grey curve)

FIG. 13 shows an overlay of gas chromatograms of the aforementioned two recombinant *E. coli* cultures. According to this figure, an additional peak at the retention time of 1-octanol (about 7.8 minutes) was observed for the culture of the recombinant *E. coli* carrying the pBBR1-CYPLR plasmid (dark gray curve) compared to the culture of the recombinant *E. coli* carrying the pBBR1-alkR plasmid (light gray curve). The result indicates that the medium-chain or long-chain alkane exists as both an inducer and a reactant for the recombinant microorganism including the CYP153A operon, where it induces the expression of cytochrome P450 with oxidative activity and also become transformed into alkanols. Therefore, the recombinant microorganisms including the CYP153A operon may be used to develop a whole-cell catalytic system that requires no additional addition of conventional inducers such as IPTG to produce the medium-chain or long-chain alkane terminal oxidation products.

Example 4

Enhancing Effect of the Alkane Transporter on the Fluorescent Protein Expression in the Recombinant AlkR-Expressing Microorganism Upon Induction with Medium-Chain or Long-Chain Alkanes Example 1 shows that the outer membrane of *E. coli* has low permeability to the medium-chain and long-chain alkanes having a carbon chain length greater than C8 (FIGS. 9A-9F), for example, only a portion of the recombinant *E. coli* was induced to express red fluorescent proteins in the presence of the straight-chain alkanes having a carbon chain length greater than C8. This characteristic might prevent the recombinant microorganism including the CYP153A operon from being induced by the medium-chain or long-chain alkanes or medium-chain or long-chain fatty acid methyl esters and producing the medium-chain or long-chain alkane terminal oxidation products. In order to promote the entry of medium-chain or long-chain alkanes into cells, the recombinant microorganism of the present invention may further express an alkane transporter. The AlkL protein of *P. putida* GPol is an exemplary alkane transporter used in this example to investigate the effects of alkane transporter expression on the uptake of medium-chain or long-chain alkanes or medium-chain or long-chain fatty acid methyl esters by the recombinant microorganisms. The AlkL protein is cytotoxic and its expression should be tightly regulated. Therefore, a rhamnose-inducible AlkL protein expression vector, that is, the psb3C5-rha-weak AlkL plasmid shown in FIG. 3, was first constructed and used to transform the recombinant *E. coli* JM109 carrying the reporter plasmid psb4K5-alkR-mRFP. The transformed *E. coli* was then cultured in LB medium, and the expression of AlkL protein was induced by adding various concentrations of rhamnose to the medium at an O.D.600 of about 0.6, which was followed by adding 1% (v/v) n-tetradecane to the medium to induce the expression of red fluorescent protein, as described in the method for alkane induction assay. At 6 hours after the induction, the mean fluorescence intensity of *E. coli* cells was measured by flow cytometry.

Figure 14:
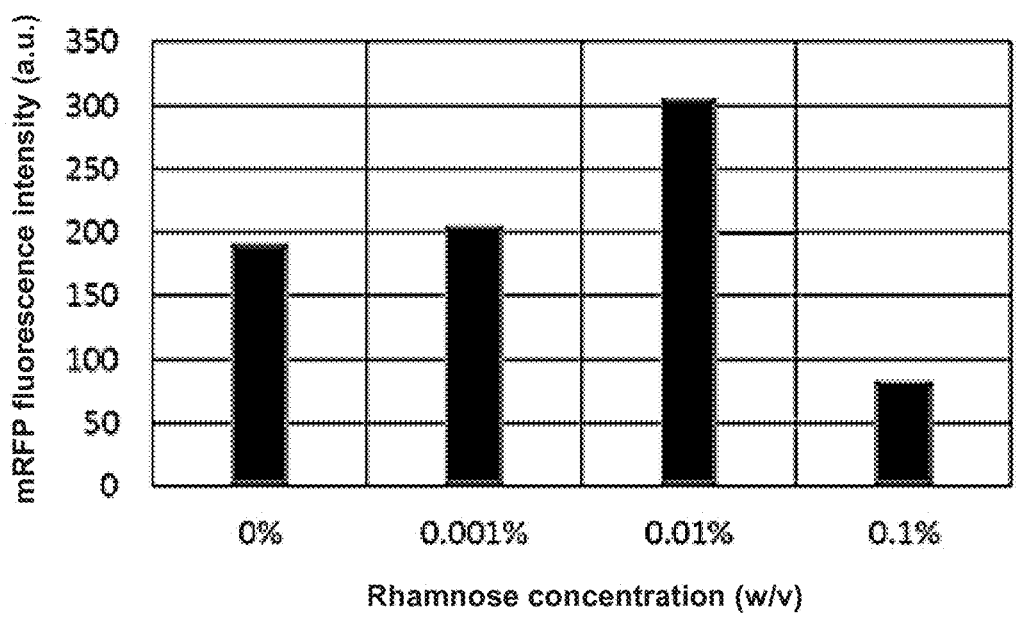
FIG. 14 shows the mean fluorescence intensity of recombinant E. coli cells carrying the psb4K5-alkR-mRFP plasmid and psb3C5-rha-weak alkL plasmid after first induction with various concentrations of rhamnose and subsequent induction with 1% n-tetradecane.

FIG. 14 shows the red fluorescence intensity (a.u.) of the aforementioned recombinant *E. coli*. According to the figure, 0.01% (w/v) rhamnose and n-tetradecane induced significantly more expression of the red fluorescent protein in the *E. coli* when compared to no rhamnose addition, indicating that the addition of 0.01% rhamnose was able to induce AlkL protein expression, thus improving the uptake of n-tetradecane into the *E. coli* cells, which in turn induced more expression of red fluorescent protein. The results show that the recombinant microorganism carrying the psb3C5-rha-weak alkL plasmid can express the functional AlkL protein under the regulation of rhamnose. Thus, such recombinant microorganism can be utilized to facilitate cellular uptake of the medium-chain or long-chain alkanes or medium-chain or long-chain fatty acid methyl esters under conditions where AlkL expression and cytotoxicity are being controlled.

The AlkL protein was also tested for the ability to promote the uptake of various medium-chain or long-chain alkanes and methyl laurate by microbial cells. The recombinant *E. coli* JM109 carrying the psb3C5-rha-weak alkL plasmid and psb4K5-alkR-mRFP plasmid was cultured in LB medium, and 0.01% (w/v) rhamnose was added to the culture at an O.D.600 of about 0.6. After 3 hours of incubation, 1% (v/v) n-octane, n-decane, n-dodecane, n-tetradecane, n-hexadecane, n-octadecane, or methyl laurate was added to induce the expression of red fluorescent protein, and the mean fluorescence intensity and fluorescence distribution of *E. coli* cells were measured by flow cytometry 6 hours after the induction. For comparison purposes, groups of recombinant *E. coli* JM109 carrying the psb3C5-rha plasmid (mock vector) and psb4K5-alkR-mRFP plasmid were treated similarly and used as control. There were also non-induced groups of recombinant *E. coli* cells that were not treated with rhamnose and any of the alkanes.

Figure 15:
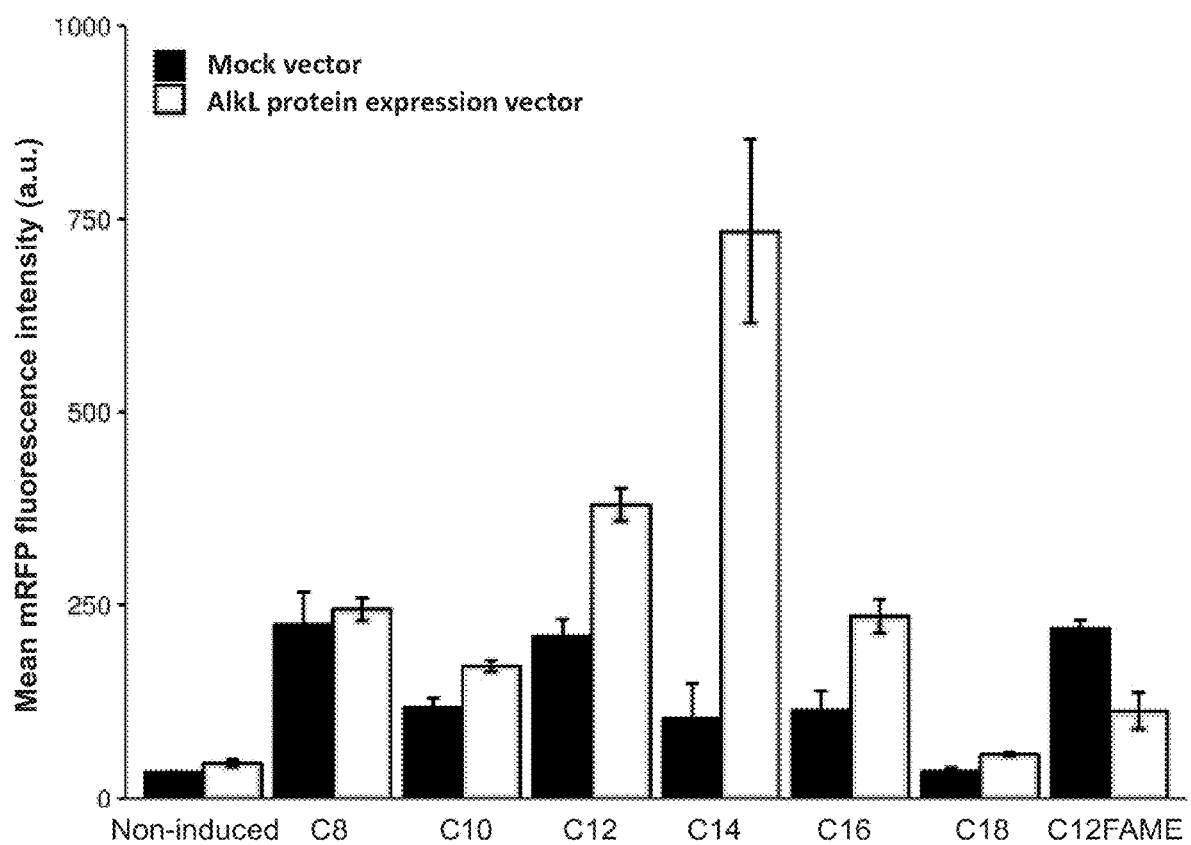
FIG. 15 shows the mean fluorescence intensity of the recombinant E. coli cells carrying the psb4K5-alkR-mRFP plasmid and psb3C5-rha-weak alkL plasmid or the recombinant E. coli cells carrying the psb3C5-rha plasmid (mock vector) and psb4K5-alkR-mRFP plasmid after first induction with 0.01% rhamnose and subsequent induction with 1% n-octane (C8), n-decane (C10), n-dodecane (C12), n-tetradecane (C14), n-hexadecane (C16), n-octadecane (C18) or methyl laurate (C12FAME)

FIG. 15 shows the red fluorescence intensity (a.u.) of the aforementioned recombinant *E. coli*. According to the figure, methyl laurate and the straight-chain alkanes having a carbon chain length between C8 and C18 were sufficient to induce significantly more expression of the red fluorescent protein in the recombinant *E. coli* of the control groups than the non-induced groups. In addition, the straight-chain alkanes having a carbon chain length between C10 and C18, particularly n-tetradecane, were more effective in inducing the expression of red fluorescent protein in the *E. coli* cells expressing both the AlkL and AlkR proteins. The results indicate that the alkane transporter promotes the entry of a variety of medium-chain and long-chain alkanes into recombinant microbial cells, thereby increasing the extent to which recombinant microorganisms are induced to express protein by medium-chain or long-chain alkanes.

Figure 16A:
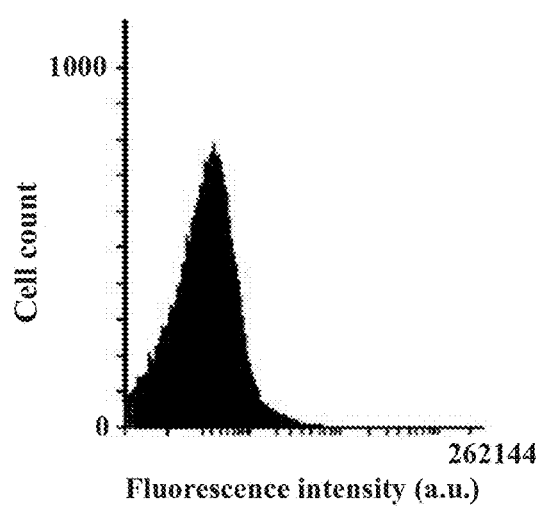
FIG. 16A shows the fluorescence distribution histograms of the recombinant E. coli cells carrying the psb3C5-rha-weak alkL plasmid and psb4K5-alkR-mRFP plasmid (white) or the recombinant E. coli cells carrying the psb3C5-rha plasmid and psb4K5-alkR-mRFP plasmid (black); the E. coli cells were first induced with 0.01% rhamnose and then induced with 1% n-octane.
Figure 16B:
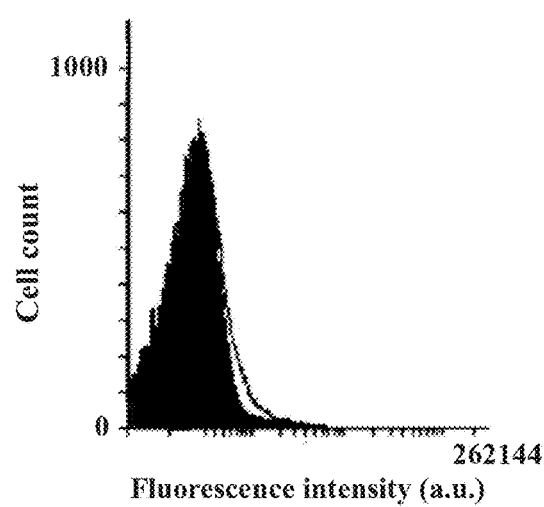
FIG. 16B shows the fluorescence distribution histograms of the recombinant E. coli cells carrying the psb3C5-rha-weak alkL plasmid and psb4K5-alkR-mRFP plasmid (white) or the recombinant E. coli cells carrying the psb3C5-rha plasmid and psb4K5-alkR-mRFP plasmid (black); the E. coli cells were first induced with 0.01% rhamnose and then induced with 1% n-decane.
Figure 16C:
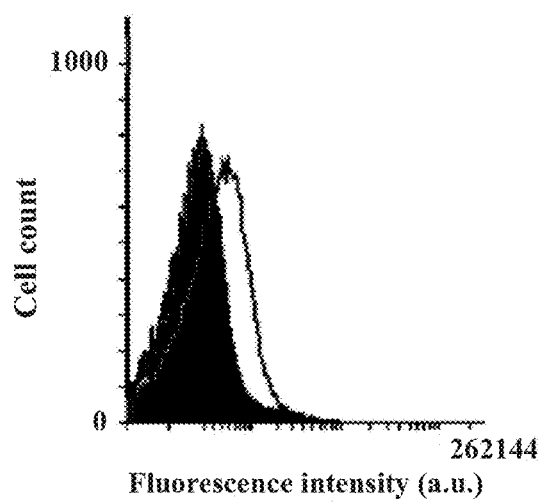
FIG. 16C shows the fluorescence distribution histograms of the recombinant E. coli cells carrying the psb3C5-rha-weak alkL plasmid and psb4K5-alkR-mRFP plasmid (white) or the recombinant E. coli cells carrying the psb3C5-rha plasmid and psb4K5-alkR-mRFP plasmid (black); the E. coli cells were first induced with 0.01% rhamnose and then induced with 1% n-dodecane.
Figure 16D:
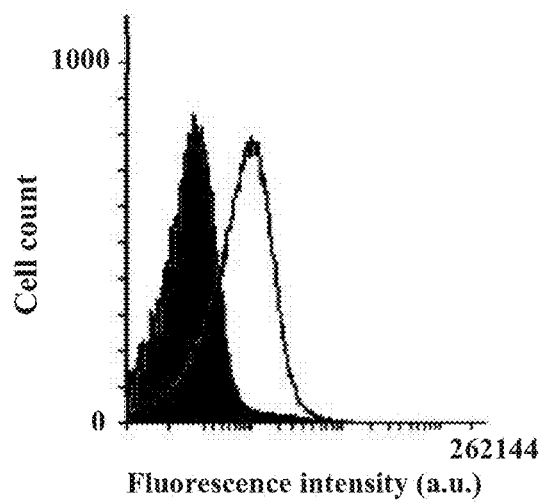
FIG. 16D shows the fluorescence distribution histograms of the recombinant E. coli cells carrying the psb3C5-rha-weak alkL plasmid and psb4K5-alkR-mRFP plasmid (white) or the recombinant E. coli cells carrying the psb3C5-rha plasmid and psb4K5-alkR-mRFP plasmid (black); the E. coli cells were first induced with 0.01% rhamnose and then induced with 1% n-tetradecane.
Figure 16E:
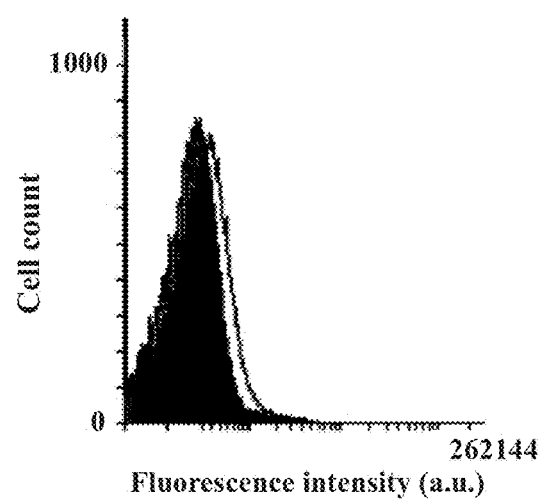
FIG. 16E shows the fluorescence distribution histograms of the recombinant E. coli cells carrying the psb3C5-rha-weak alkL plasmid and psb4K5-alkR-mRFP plasmid (white) or the recombinant E. coli cells carrying the psb3C5-rha plasmid and psb4K5-alkR-mRFP plasmid (black); the E. coli cells were first induced with 0.01% rhamnose and then induced with 1% n-hexadecane.
Figure 16F:
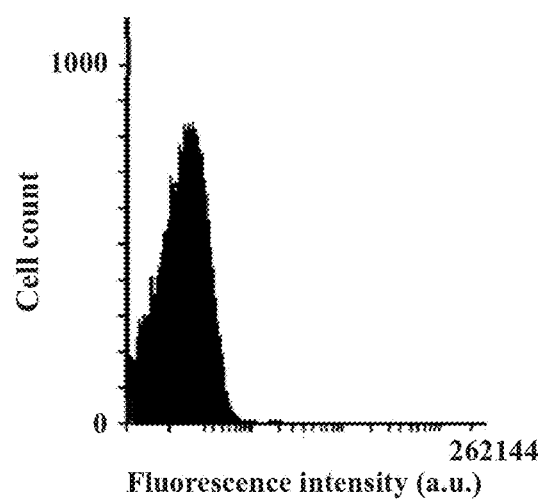
FIG. 16F shows the fluorescence distribution histograms of the recombinant E. coli cells carrying the psb3C5-rha-weak alkL plasmid and psb4K5-alkR-mRFP plasmid (white) or the recombinant E. coli cells carrying the psb3C5-rha plasmid and psb4K5-alkR-mRFP plasmid (black); the E. coli cells were not induced with rhamnose and alkanes.

FIGS. 16A-16E show the fluorescence distribution histograms of the control groups (black) and the recombinant *E. coli* carrying the psb3C5-rha-weak alkL plasmid and psb4K5-alkR-mRFP plasmid (white), both of which were first induced with 0.01% (w/v) rhamnose for 3 hours and then induced for 6 hours with 1% alkanes of various carbon chain lengths; FIG. 16F shows the fluorescence distribution histograms of the non-induced groups. According to FIGS. 16A-16F, AlkL protein expression led to the expression of red fluorescent protein in more *E. coli* cells that were induced by straight-chain alkanes having a carbon chain length greater than C8, and thus the corresponding peaks were found to be toward the high-fluorescence intensity side of the histograms. The results show that the alkane transporter effectively increases the number of recombinant microbial cells that can be induced by medium-chain or long-chain alkanes.

Example 5

Preparation of Alkanols and Alkanediols Using Recombinant *E. coli* 5.1 Small-Scale Production of 1-Dodecanol To illustrate the method of preparing medium-chain or long-chain alkane terminal oxidation products that applies the growing cell culture, a recombinant *E. coli* JM109 carrying the pBBR1-CYPLR plasmid and psb3C5-rha-weak alkL plasmid was described as an exemplary whole-cell catalytic system. First, the recombinant *E. coli* was inoculated in LB medium and cultured overnight at 37° C. with agitation at 125-150 rpm. The overnight culture was diluted 1000-fold in 10 mL of LB medium contained in a 50 mL Hinton's flask and cultured at 37° C. 0.01% (w/v) rhamnose and 100 μL n-dodecane were added to the culture at an O.D.600 of about 0.6 for induction and biotransformation. It was verified by gas chromatography/mass spectrometry that 1-dodecanol was present in the culture after 6 or 12 hours (data not shown). This result shows that the medium-chain or long-chain alkane terminal oxidation products can be successfully produced by the whole-cell catalytic system of the present invention without the need of additionally adding conventional inducers such as IPTG and changing medium.
5.2 Production of 1-Dodecanol and 1-Tetradecanol Using a Bioreactor In order to increase product production, a fed-batch culture of recombinant microorganisms was performed in a small bioreactor to produce medium-chain or long-chain alkane terminal oxidation products. The recombinant *E. coli* JM109 carrying the pBBR1-CYPLR plasmid and psb3C5-rha-weak alkL plasmid was cultured in 3 mL LB medium at 37° C., and then transferred into a 500 mL Hinton's flask containing 100 mL of LB medium for overnight culture at 37° C. and 125-150 rpm. The overnight culture was inoculated to a 5 L bioreactor FS-01-110 (Major Science) containing 2 L of TB medium. The TB medium contained 30 g glucose or 30 g glycerol as a carbon source. The culture temperature was about 37° C., the pH value was about 7.0-7.2, and the dissolved oxygen was maintained at about 40% by adjusting the stirring speed between 300-1000 rpm. The pH value of the medium was adjusted using 8 N sodium hydroxide and 1 N hydrochloric acid. At the time a rapid rise in the pH value of the medium was observed, indicating that the carbon source was used up by E. coli, a feed medium containing 30 g yeast extract and either 50% (w/v) glucose or 80% (v/v) glycerin per liter was added. 0.1% (w/v) rhamnose was added to the culture at about 5-6 hours after the bacterial inoculation, and 200 mL of n-dodecane or n-tetradecane was added for biotransformation at 1-2 hours after the rhamnose addition. The temperature of the bioreactor was dropped to about 25° C. after rhamnose addition. Samples of the bacterial culture were collected periodically during the aforementioned process for determining the dry cell mass of bacteria. Also, the composition of the medium was analyzed by gas chromatography/mass spectrometry and quantitation was done by gas chromatography.

Figure 17:
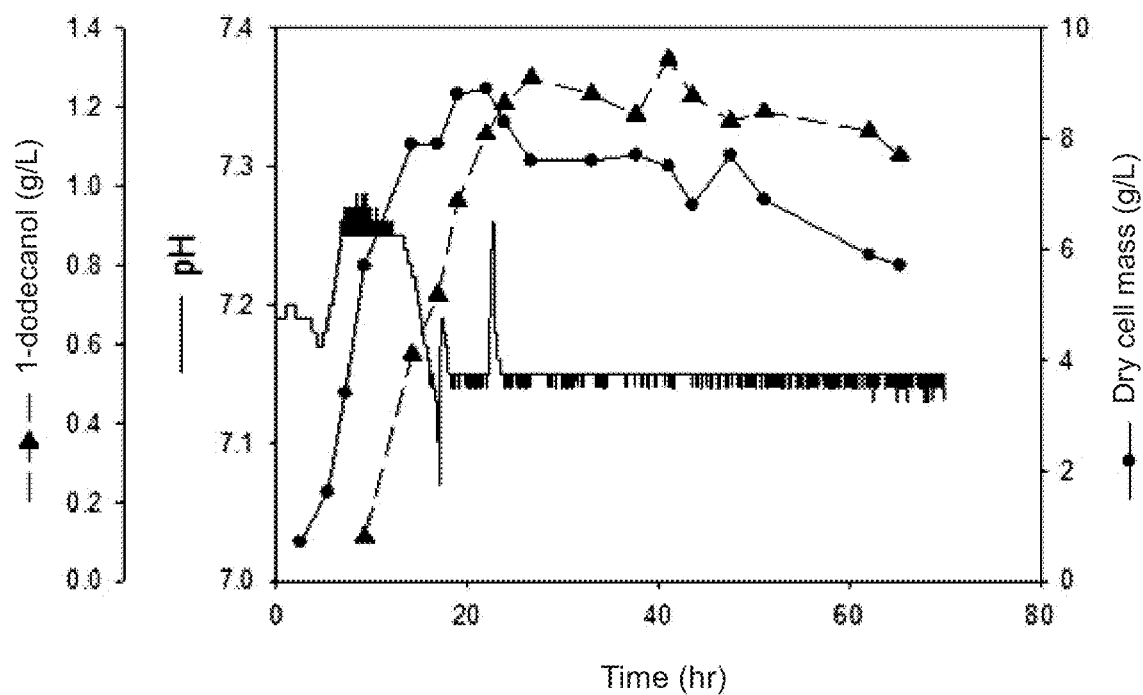
FIG. 17 shows the variation in product concentration, pH value of the medium, and dry cell mass during n-dodecane biotransformation by culturing the recombinant E. coli cells carrying the pBBR1-CYPLR plasmid and psb3C5-rha-weak alkL plasmid in the glucose-containing TB medium.
Figure 18:
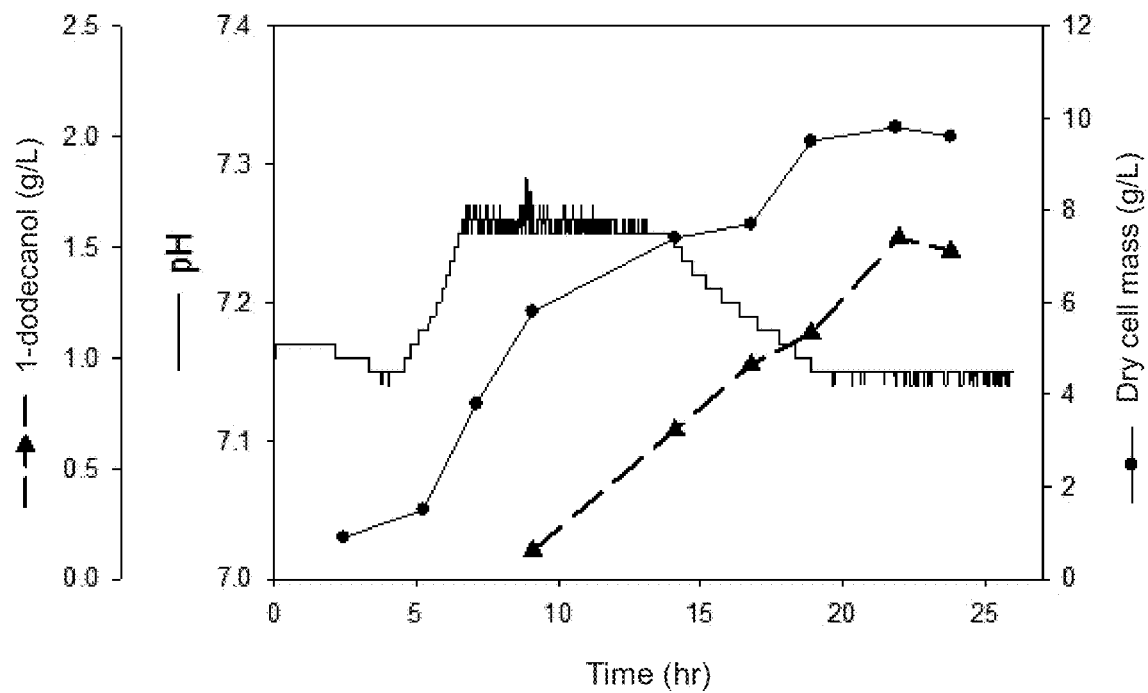
FIG. 18 shows the variation in product concentration, pH value of the medium, and dry cell mass during n-dodecane biotransformation by culturing the recombinant E. coli cells carrying the pBBR1-CYPLR plasmid and psb3C5-rha-weak alkL plasmid in the glycerol-containing TB medium.

FIG. 17 shows the result of n-dodecane biotransformation by culturing the recombinant E. coli carrying the aforementioned two plasmids in the glucose-containing TB medium; FIG. 18 shows the result of n-dodecane biotransformation by culturing the recombinant E. coli carrying the aforementioned two plasmids in the glycerol-containing TB medium. According to FIG. 17, approximately 1.3 g/L of 1-dodecanol was obtained after about 27 hours of biotransformation. According to FIG. 18, approximately 1.5 g/L of 1-dodecanol was obtained after about 23 hours of biotransformation. These results show that the use of glycerol as carbon source is more beneficial for n-dodecanol production by recombinant E. coli.

Figure 19:
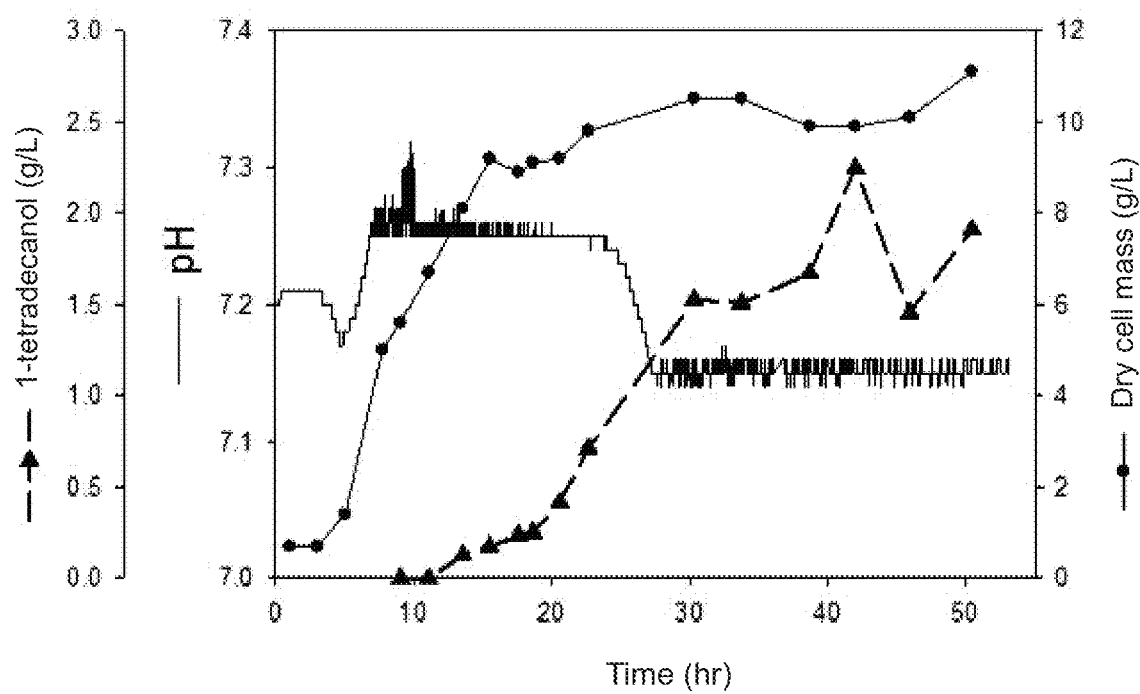
FIG. 19 shows the variation in product concentration, pH value of the medium, and dry cell mass during n-tetradecane biotransformation by culturing the recombinant E. coli cells carrying the pBBR1-CYPLR plasmid and psb3C5-rha-weak alkL plasmid in the glycerol-containing TB medium.

FIG. 19 shows the result of n-tetradecane biotransformation by culturing the recombinant E. coli carrying the aforementioned two plasmids in the glycerol-containing TB medium. According to this figure, approximately 2.3 g/L of 1-tetradecanol was obtained after about 41 hours of biotransformation.

5.3 Production of 1,12-Dodecanediol Using a Bioreactor with the Addition of Antibiotics Given previous studies showing that the addition of antibiotics during bacterial culture helps maintain plasmid stability (data not shown), this example describes the production of medium-chain or long-chain alkane terminal oxidation products in a small bioreactor with the addition of antibiotics. The recombinant E. coli JM109 carrying the pBBR1-CYPLR plasmid and psb3C5-rha-weak alkL plasmid was cultured at 37° C. and 125-150 rpm for 24 hours in 3 mL of LB medium containing 50 µg/mL kanamycin and 50 µg/mL chloramphenicol. 1 mL of the bacterial culture was then transferred to a 500 mL Hinton' flask containing 100 mL of LB medium (supplemented with kanamycin and chloramphenicol each at 50 µg/mL) and incubated at 37° C. and 125-150 rpm for 24 hours. Thereafter, 15 mL of the aforementioned bacterial culture was inoculated to a 5 L bioreactor containing 1.5 L of TB medium at an inoculation rate of 1% (v/v). The TB medium contained 30 g glycerol as a carbon source, and both kanamycin and chloramphenicol were added to the medium at 50 µg/mL. The culture temperature was 37° C., the pH value was about 7.0-7.2, and the dissolved oxygen was maintained at 20% or more by adjusting the stirring speed between 300-720 rpm. About 9 hours after the bacterial inoculation, a rapid rise in the pH value of the medium was observed, indicating that the carbon source was used up by E. coli, and a feed medium containing 30 g yeast extract and 150 g glycerol per liter was added. About 3 hours after the feed (12 hours after the bacterial inoculation), 1.5 g rhamnose and 30 g 1-dodecanol were added to the culture for the first induction and biotransformation. After the rhamnose addition, the bioreactor was cooled to 25° C. and the culture was continued for 48 hours. Approximately 40 hours after the bacterial inoculation, 75 mg kanamycin, 75 mg chloramphenicol, 1.5 g rhamnose, and 30 g 1-dodecanol were added for the second induction. Samples of the bacterial culture were collected periodically during the aforementioned process for determining the dry cell mass of bacteria and bacterial count in log value. Also, the composition of the medium was analyzed by gas chromatography/mass spectrometry and quantitation was done by gas chromatography.

Figure 20:
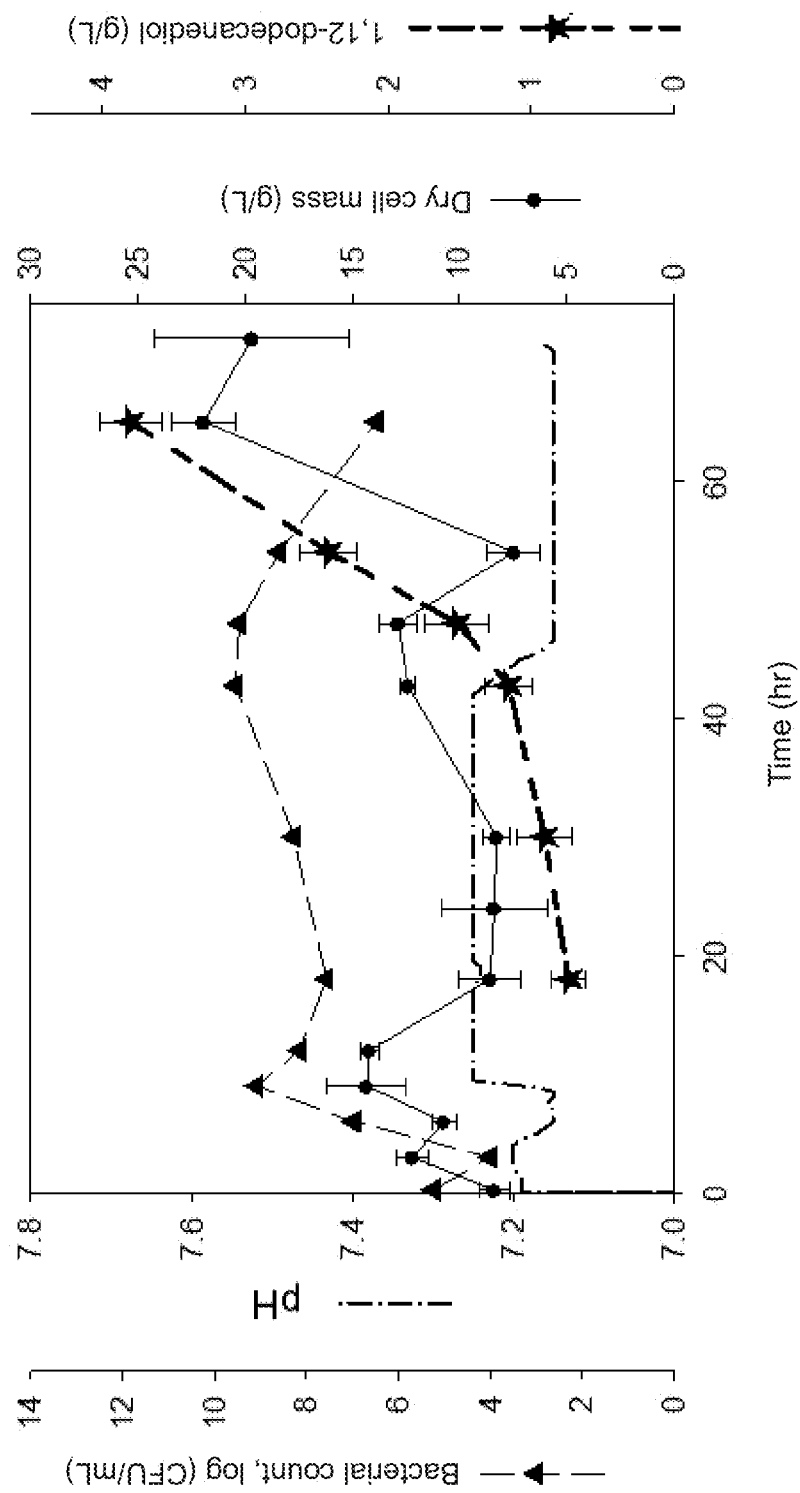
FIG. 20 shows the variation in product concentration, pH value of the medium, bacterial count in log value, and dry cell mass during 1-dodecanol biotransformation by culturing the recombinant E. coli cells carrying the pBBR1-CYPLR plasmid and psb3C5-rha-weak alkL plasmid in the TB medium containing glycerol and antibiotics.

FIG. 20 shows the result of 1-dodecanol biotransformation by culturing the recombinant E. coli carrying the aforementioned two plasmids in the TB medium containing glycerol and antibiotics. According to FIG. 20, the bacterial count before the induction was 9.08 log (CFU/mL), whereas the bacterial count decreased significantly to 6 log (CFU/mL) at 24 hours after the induction. Though the bacterial count increased to 9.54 log (CFU/mL) at 40 hours after bacterial inoculation, it decreased again to 6 log (CFU/mL) after the second induction. However, both the dry cell mass of bacteria and the concentration of 1,12-dodecanediol significantly increased. The dry cell mass of bacteria reached 21.94 g/L at 65 hours after bacterial inoculation; the concentration of 1,12-dodecanediol increased steadily after induction and reached 3.76 g/L at 71.5 hours after bacterial inoculation. Furthermore, only a small amount of dodecanal was detected in the medium, indicating that the whole-cell catalytic system of the present invention has low overoxidation activity.

To prepare an alcohol amine using the whole-cell catalytic system of the present invention, in one embodiment, a recombinant E. coli JM109 including the CYP153A operon was transformed with a gene encoding transaminase and then cultured according to procedures similar to Example 5.3, where the bacteria were induced to undergo biotransformation with medium-chain or long-chain alkanes to produce the alcohol amine.

Example 6

Preparation of 1-Dodecanoic Acid and 1,12-Dodecanedioic Acid Using Recombinant P. putida GPo1

A recombinant P. putida GPo1 transformed with the pBBR1-CYPLR plasmid was used as an exemplary whole-cell catalytic system to illustrate the steps of preparing medium-chain alkanoic acids and medium-chain alkane dioic acids according to the method of the present invention. The recombinant P. putida GPo1 had been verified to express the AlkR protein and the CYP153A, ferredoxin, and ferredoxin reductase from M. aquaeoli VT8. Furthermore, in order to avoid degradation of the fatty acid products via the β-oxidation pathway and to enhance the terminal oxidation of n-dodecane, the β-oxidation pathway of the recombinant P. putida GPo1 was blocked by genetic engineering techniques, and the genes encoding the alkane hydroxylase AlkB system on the OCT plasmid was replaced by the genes encoding the alkane hydroxylase AlkB2 system of P. aeruginosa PAO1.

The aforementioned recombinant P. putida GPo1 was cultured overnight at 30° C. and 125-150 rpm in 3 mL of LB medium containing 50 µg/mL kanamycin. 1 mL of the aforementioned bacterial culture was then transferred to a 500 mL Hinton' flask containing 100 mL of LB medium (supplemented with 50 µg/mL kanamycin) and incubated at 30° C. and 125-150 rpm for 12 hours. Thereafter, the aforementioned bacterial culture was inoculated to a 5 L bioreactor containing 1.5 L of LB medium at an inoculation rate of 1% (v/v). The LB medium was supplemented with 50 μg/mL kanamycin. The culture temperature was 30° C., the pH value was maintained at about 7, and the dissolved oxygen was maintained at 20% or more by adjusting the stirring speed between 300-960 rpm. The pH value of the medium was adjusted using 4 N sodium hydroxide and 4 N hydrochloric acid. About 50 mL n-octane and about 100 mL n-dodecane were added to the culture for induction and biotransformation about 6 hours after the bacterial inoculation, wherein n-octane was used to induce the expression of the AlkB2 system. Samples of the bacterial culture were collected periodically during the aforementioned process for determining the dry cell mass of bacteria. Also, the composition of the medium was analyzed by gas chromatography/mass spectrometry and quantitation was done by gas chromatography.

Figure 21:
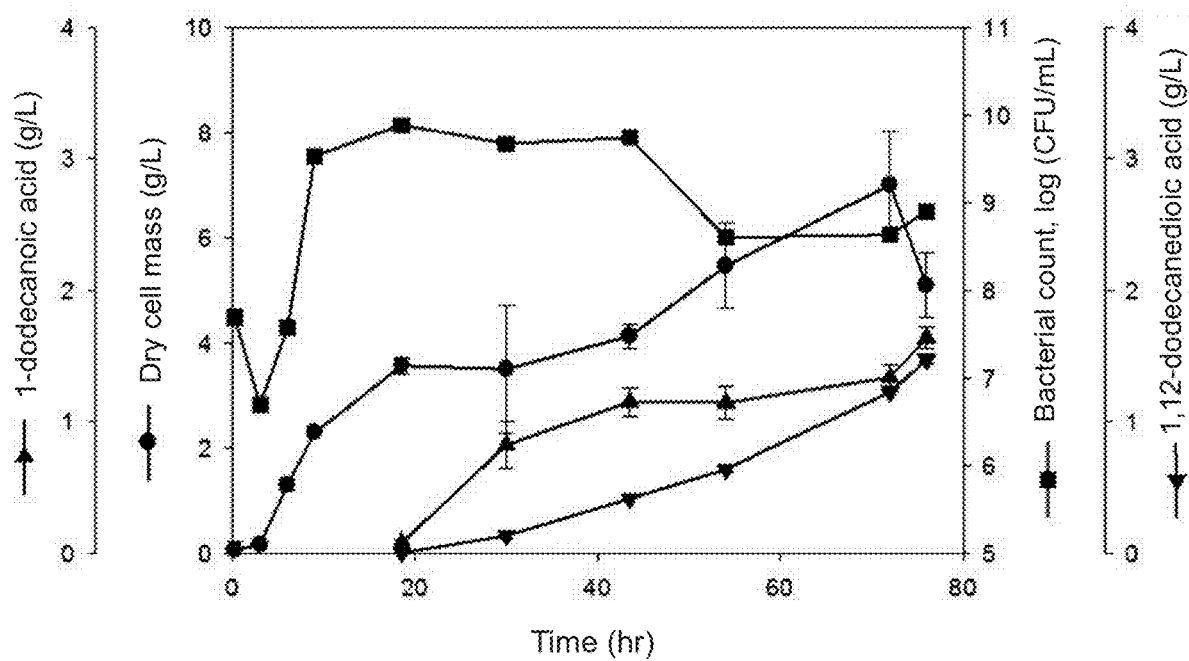
FIG. 21 shows the variation in product concentration, bacterial count in log value, and dry cell mass during n-dodecane biotransformation by culturing the recombinant Pseudomonas putida GPol cells carrying the pBBR1-CYPLR plasmid in the antibiotic-containing LB medium.

FIG. 21 shows the result of n-dodecane biotransformation by culturing the aforementioned recombinant P. putida GPol in the antibiotic-containing LB medium. According to FIG. 21, the dry cell mass increased with time and reached 7.0 g/L at 76 hours after bacterial inoculation. The concentrations of 1-dodecanoic acid and 1,12-dodecanedioic acid increased steadily, reaching 1.64 g/L and 1.47 g/L, respectively, at 76 hours after bacterial inoculation.

Example 7

Preparation of 12-Carboxyl Lauric Acid Methyl Ester Using Recombinant P. putida GPol To illustrate the method of preparing medium-chain or long-chain fatty acid methyl ester (FAME) terminal oxidation products such as α,ω-dicarboxylic acid methyl esters, a recombinant P. putida GPol as described in EXAMPLE 6 was prepared. The recombinant P. putida GPol was cultured overnight at 30° C. with agitation at 125-150 rpm in 3 mL of LB medium containing 50 μg/mL kanamycin. 1 mL of the aforementioned bacterial culture was then transferred to a 500 mL Hinton's flask containing 100 mL of LB medium supplemented with 50 μg/mL kanamycin and incubated at 30° C. and 125-150 rpm. 3% (v/v) methyl laurate and 3% (v/v) n-dodecane were added to the bacterial culture at an O.D.600 of about 1 for induction and biotransformation.

After about 60 hours of biotransformation, 0.336 g/L of 12-carboxyl lauric acid methyl ester was detected in the culture by gas chromatography, indicating that FAME terminal oxidation products can be successfully produced using the whole-cell catalytic system of the present invention.

In conclusion, based on the results of alkane induction assay performed with the repaired CYP153A operon of M. aquaeoli VT8, the present invention provides a method of activating gene expression by using the AlkR protein having 90% or more sequence identity to SEQ ID NO:45. The AlkR protein is capable of sensing the presence of medium-chain or long-chain alkanes or medium-chain or long-chain fatty acid methyl esters and activating gene expression, and thus can be used to develop a whole-cell catalytic system regulated by medium-chain or long-chain alkanes or medium-chain or long-chain fatty acid methyl esters, for example, a recombinant E. coli or a recombinant P. putida expressing the AlkR protein and a cytochrome P450. Because the whole-cell catalytic system of the present invention utilizes the medium-chain or long-chain alkanes or medium-chain or the long-chain fatty acid methyl esters as both an inducer and a reactant, it is suitable for producing the medium-chain or long-chain alkane terminal oxidation products in growing cell cultures. Therefore, the medium-chain or long-chain alkanes or medium-chain or the long-chain fatty acid methyl esters can be easily converted to the medium-chain or long-chain alkane terminal oxidation products by the preparation method of the present invention without the need to additionally supply the conventional inducers such as IPTG and to change the culture medium. In addition, when the whole-cell catalytic system of the present invention is employed selectively with an appropriate alkane oxidation system, such as the reconstructed CYP153A operon of the M. aquaeoli VT8, the resulting biotransformation owns the advantages of finely regulated expression of CYP153A, less overoxidation of the products, and no product inhibition.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method of activating gene expression, comprising a step of contacting a recombinant microbial cell with a medium-chain or long-chain alkane or a medium-chain or long-chain fatty acid methyl ester;
wherein the recombinant microbial cell expresses a protein having 90% or more sequence identity to SEQ ID NO:45 and comprises a gene for activated expression;
wherein the recombinant microbial cell further expresses an alkane transporter and an alkane monooxygenase;
wherein the alkane monooxygenase is a cytochrome P450, the cytochrome P450 consists of a CYP153A, a ferredoxin, and a ferredoxin reductase;
wherein the CYP153A, the ferredoxin, and the ferredoxin reductase are derived from *Marinobacter aquaeoli* VT8, the CYP153A is reconstructed to exclude a transposon at a position corresponding to an amino terminus of the ferredoxin; and
wherein the alkane transporter is an AlkL protein derived from *Pseudomonas putida*, and the gene expression is activated without adding isopropyl β-D-1-thiogalactopyranoside (IPTG) or dicyclopropylketone (DCPK) as an inducer.

2. The method of claim 1, wherein the medium-chain or long-chain alkane is a straight-chain alkane having a carbon chain length of C8 or greater.

3. The method of claim 1, wherein the medium-chain or long-chain fatty acid methyl ester is a straight-chain saturated fatty acid methyl ester having a carbon chain length of C8 or greater.

4. The method of claim 3, wherein the straight-chain saturated fatty acid methyl ester is methyl laurate.

5. The method of claim 1, wherein the gene encodes a cytochrome P450.

6. A whole-cell catalytic system regulated by a medium-chain or long-chain alkane or a medium-chain or long-chain fatty acid methyl ester, comprising a recombinant microbial cell expressing a protein having 90% or more sequence identity to SEQ ID NO:45 and an alkane monooxygenase;
wherein the recombinant microbial cell further expresses an alkane transporter, the alkane transporter is an AlkL protein derived from *Pseudomonas putida*, and the whole-cell catalytic system is regulated without adding isopropyl β-D-1-thiogalactopyranoside (IPTG) or dicyclopropylketone (DCPK) as an inducer; and
wherein the alkane monooxygenase is a cytochrome P450, the cytochrome P450 consists of a CYP153A, a ferredoxin, and a ferredoxin reductase, the CYP153A, the ferredoxin, and the ferredoxin reductase are derived from *Marinobacter aquaeoli* VT8, and the CYP153A is reconstructed to exclude a transposon at a position corresponding to an amino terminus of the ferredoxin.

7. A method of preparing a medium-chain or long-chain alkane terminal oxidation product, comprising the following steps of:
(a) providing a recombinant microorganism, comprising a first gene encoding an alkane monooxygenase, and a second gene encoding a protein having 90% or more sequence identity to SEQ ID NO:45;
(b) incubating the recombinant microorganism in a culture medium containing a carbon source; and
(c) adding a medium-chain or long-chain alkane or a medium-chain or long-chain fatty acid methyl ester to the culture medium for a predetermined period of time to obtain the medium-chain or long-chain alkane terminal oxidation product, wherein the recombinant microorganism further comprises a gene encoding an alkane transporter, the alkane transporter is an AlkL protein derived from *Pseudomonas putida*, and the medium-chain or long-chain alkane terminal oxidation product is prepared without adding isopropyl β-D-1-thiogalactopyranoside (IPTG) or dicyclopropylketone (DCPK) as an inducer;
wherein the alkane monooxygenase is a cytochrome P450, the cytochrome P450 consists of a CYP153A, a ferredoxin, and a ferredoxin reductase, the CYP153A, the ferredoxin, and the ferredoxin reductase are derived from *Marinobacter aquaeoli* VT8, and the CYP153A is reconstructed to exclude a transposon at a position corresponding to an amino terminus of the ferredoxin.

8. The method of claim 7, wherein the medium-chain or long-chain alkane is a straight-chain alkane having a carbon chain length of C8 or greater.

9. The method of claim 7, wherein the medium-chain or long-chain fatty acid methyl ester is a straight-chain saturated fatty acid methyl ester having a carbon chain length of C8 or greater.

10. The method of claim 9, wherein the straight-chain saturated fatty acid methyl ester having a carbon chain length is methyl laurate.

11. The method of claim 7, wherein the medium-chain or long-chain alkane terminal oxidation product is an alkanol, an alkanediol, an alkanoic acid, an alkane dioic acid, a dicarboxylic acid methyl ester, an alcohol acid, or an alcohol amine having a carbon chain length of C8 or greater.

12. The method of claim 7, wherein the expression of the alkane transporter is regulated by rhamnose.

* * * * *